(12) United States Patent
Lee et al.

(10) Patent No.: US 12,191,304 B2
(45) Date of Patent: Jan. 7, 2025

(54) METHOD OF MANUFACTURING A SEMICONDUCTOR DEVICE AND A SEMICONDUCTOR DEVICE

(71) Applicant: TAIWAN SEMICONDUCTOR MANUFACTURING COMPANY, LTD., Hsinchu (TW)

(72) Inventors: Tung Ying Lee, Hsinchu (TW); Ziwei Fang, Hsinchu (TW); Yee-Chia Yeo, Hsinchu (TW); Meng-Hsuan Hsiao, Hsinchu (TW)

(73) Assignee: TAIWAN SEMICONDUCTOR MANUFACTURING COMPANY, LTD., Hsinchu (TW)

( * ) Notice: Subject to any disclaimer, the term of this patent is extended or adjusted under 35 U.S.C. 154(b) by 0 days.

(21) Appl. No.: 18/200,331

(22) Filed: May 22, 2023

(65) Prior Publication Data

US 2023/0299084 A1    Sep. 21, 2023

Related U.S. Application Data

(60) Division of application No. 17/322,717, filed on May 17, 2021, now Pat. No. 11,695,006, which is a
(Continued)

(51) Int. Cl.
*H01L 29/78*    (2006.01)
*H01L 21/02*    (2006.01)
(Continued)

(52) U.S. Cl.
CPC .... *H01L 27/0886* (2013.01); *H01L 21/02532* (2013.01); *H01L 21/76802* (2013.01);
(Continued)

(58) Field of Classification Search
CPC .......... H01L 27/0886; H01L 21/02532; H01L 21/76802; H01L 21/76831;
(Continued)

(56) References Cited

U.S. PATENT DOCUMENTS 5,902,124 A    5/1999    Hong
7,851,291 B2   12/2010   Shifren et al.
(Continued)

FOREIGN PATENT DOCUMENTS

KR    10-2015-0128104 A    11/2015
KR    10-2016-0093534 A    8/2016

OTHER PUBLICATIONS

Notice of Allowance issued in U.S. Appl. No. 15/602,807, dated Feb. 27, 2018.
(Continued)

*Primary Examiner* — Shahed Ahmed
(74) *Attorney, Agent, or Firm* — STUDEBAKER & BRACKETT PC

(57) ABSTRACT

In a method of forming a FinFET, a first sacrificial layer is formed over a source/drain structure of a FinFET structure and an isolation insulating layer. The first sacrificial layer is recessed so that a remaining layer of the first sacrificial layer is formed on the isolation insulating layer and an upper portion of the source/drain structure is exposed. A second sacrificial layer is formed on the remaining layer and the exposed source/drain structure. The second sacrificial layer and the remaining layer are patterned, thereby forming an opening. A dielectric layer is formed in the opening. After the dielectric layer is formed, the patterned first and second sacrificial layers are removed to form a contact opening over the source/drain structure. A conductive layer is formed in the contact opening.

20 Claims, 25 Drawing Sheets

Related U.S. Application Data continuation of application No. 15/988,624, filed on May 24, 2018, now Pat. No. 11,007,005, which is a division of application No. 15/602,807, filed on May 23, 2017, now Pat. No. 10,008,497.

(60) Provisional application No. 62/427,705, filed on Nov. 29, 2016.

(51) Int. Cl.

| | |
|---|---|
| *H01L 21/768* | (2006.01) |
| *H01L 21/8234* | (2006.01) |
| *H01L 27/088* | (2006.01) |
| *H01L 29/06* | (2006.01) |
| *H01L 29/08* | (2006.01) |
| *H01L 29/165* | (2006.01) |
| *H01L 29/49* | (2006.01) |
| *H01L 29/66* | (2006.01) |
| *H01L 29/167* | (2006.01) |
| *H01L 29/417* | (2006.01) |
| *H01L 29/51* | (2006.01) |

(52) U.S. Cl.
CPC .. *H01L 21/76831* (2013.01); *H01L 21/76877* (2013.01); *H01L 21/76897* (2013.01); *H01L 21/823431* (2013.01); *H01L 21/823437* (2013.01); *H01L 29/0649* (2013.01); *H01L 29/0847* (2013.01); *H01L 29/165* (2013.01); *H01L 29/4958* (2013.01); *H01L 29/4966* (2013.01); *H01L 29/665* (2013.01); *H01L 29/66545* (2013.01); *H01L 29/66795* (2013.01); *H01L 29/7848* (2013.01); *H01L 29/785* (2013.01); *H01L 21/823475* (2013.01); *H01L 29/167* (2013.01); *H01L 29/41791* (2013.01); *H01L 29/495* (2013.01); *H01L 29/517* (2013.01); *H01L 29/518* (2013.01); *H01L 29/7833* (2013.01)

(58) Field of Classification Search
CPC ....... H01L 21/76877; H01L 21/823431; H01L 21/823437; H01L 21/823475; H01L 29/0649; H01L 29/0847; H01L 29/165; H01L 29/665; H01L 29/66545; H01L 29/7848; H01L 29/785–7856; H01L 29/66795–66818; H01L 2029/7857–7858; H01L 29/41791; H01L 29/04–045; H01L 29/7839; H01L 29/806; H01L 21/28247

See application file for complete search history.

(56) References Cited

U.S. PATENT DOCUMENTS

| | | | |
|---|---|---|---|
| 8,772,109 B2 | 7/2014 | Colinge | |
| 8,785,285 B2 | 7/2014 | Tsai et al. | |
| 8,816,444 B2 | 8/2014 | Wann et al. | |
| 8,823,065 B2 | 9/2014 | Wang et al. | |
| 8,860,148 B2 | 10/2014 | Hu et al. | |
| 9,105,490 B2 | 8/2015 | Wang et al. | |
| 9,236,267 B2 | 1/2016 | De et al. | |
| 9,236,300 B2 | 1/2016 | Liaw | |
| 9,324,820 B1 | 4/2016 | Kelly et al. | |
| 9,412,660 B1* | 8/2016 | Xie | H01L 21/76834 |
| 9,466,570 B1* | 10/2016 | Cheng | H01L 29/41791 |
| 9,520,482 B1 | 12/2016 | Chang et al. | |
| 9,576,814 B2 | 2/2017 | Wu et al. | |
| 9,741,615 B1 | 8/2017 | Zang et al. | |
| 2002/0038997 A1* | 4/2002 | Sakai | H01L 21/67236 445/24 |
| 2011/0014769 A1 | 1/2011 | Pouydebasque et al. | |
| 2014/0027816 A1 | 1/2014 | Cea et al. | |
| 2015/0035023 A1* | 2/2015 | Kim | H01L 29/66795 257/288 |
| 2016/0181399 A1 | 6/2016 | Jun et al. | |
| 2016/0190325 A1 | 6/2016 | Liu et al. | |
| 2017/0345825 A1 | 11/2017 | Park et al. | |
| 2018/0108660 A1* | 4/2018 | Pranatharthiharan | H01L 29/165 |

OTHER PUBLICATIONS

Non-Final Office Action issued in U.S. Appl. No. 15/988,624, dated Sep. 1, 2020.

Notice of Allowance issued in U.S. Appl. No. 15/988,624, dated Jan. 22, 2021.

Non-Final Office Action issued in U.S. Appl. No. 17/322,717, dated Sep. 15, 2022.

Notice of Allowance issued in U.S. Appl. No. 17/322,717, dated Feb. 22, 2023.

* cited by examiner

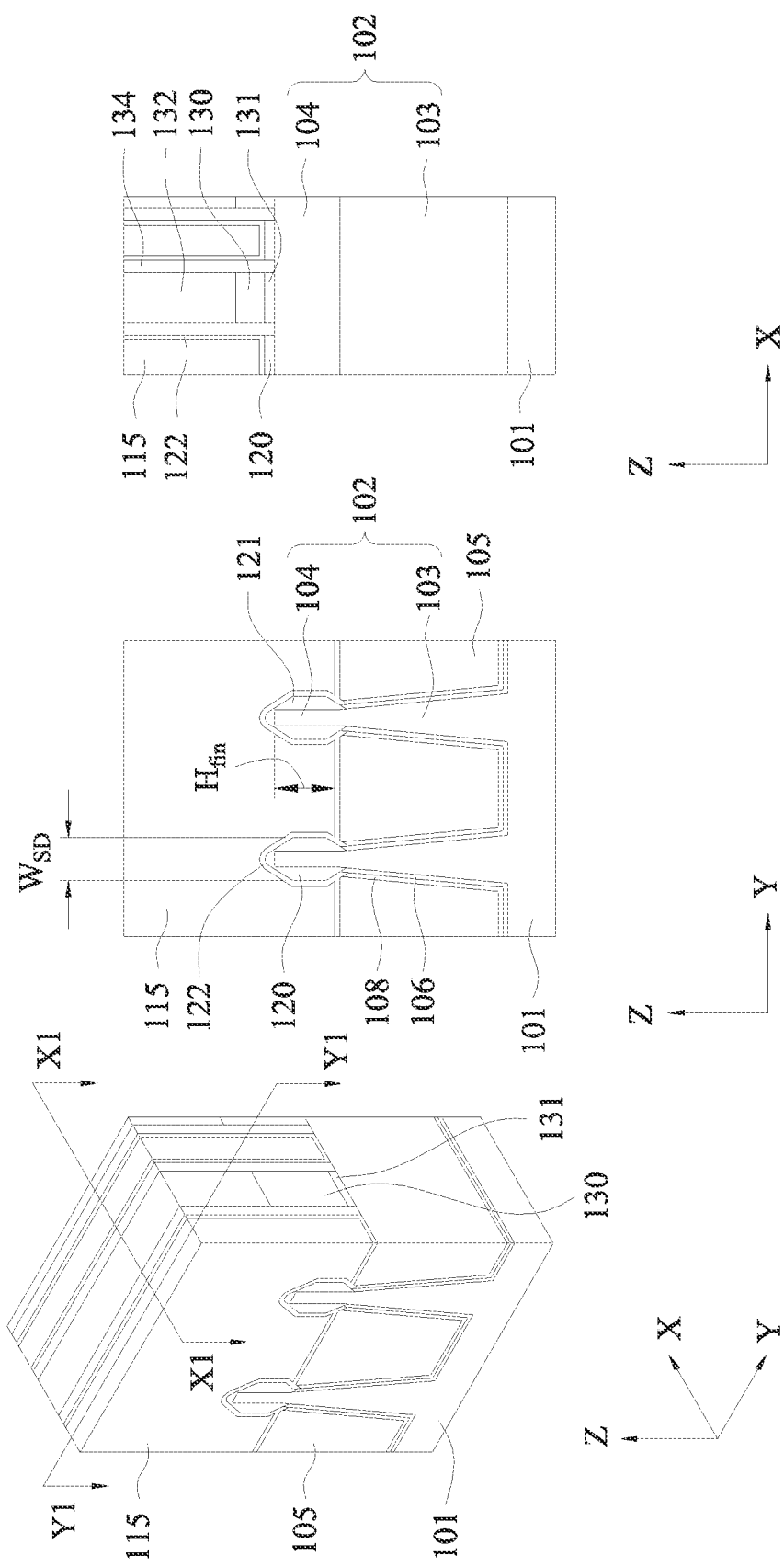

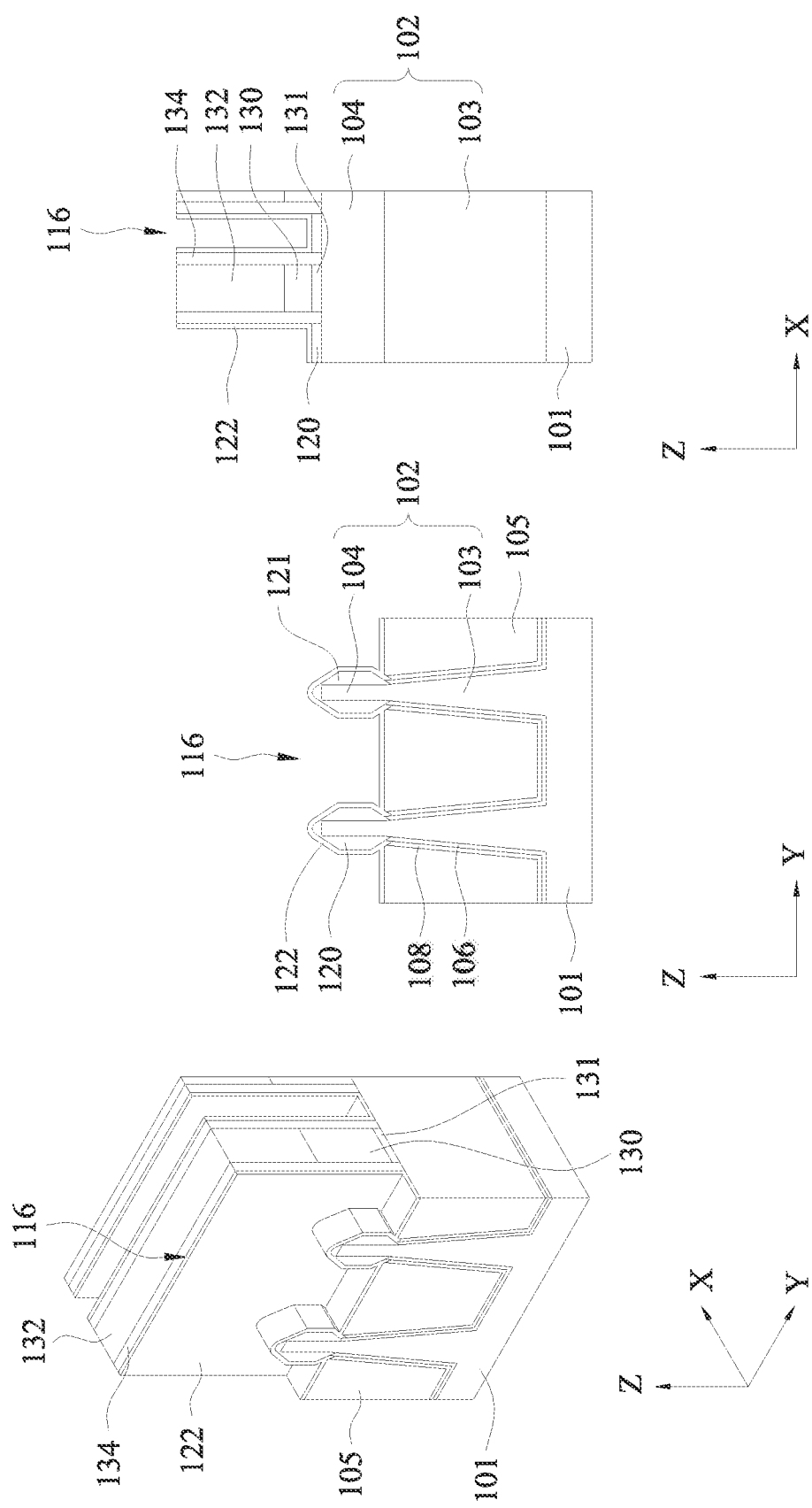

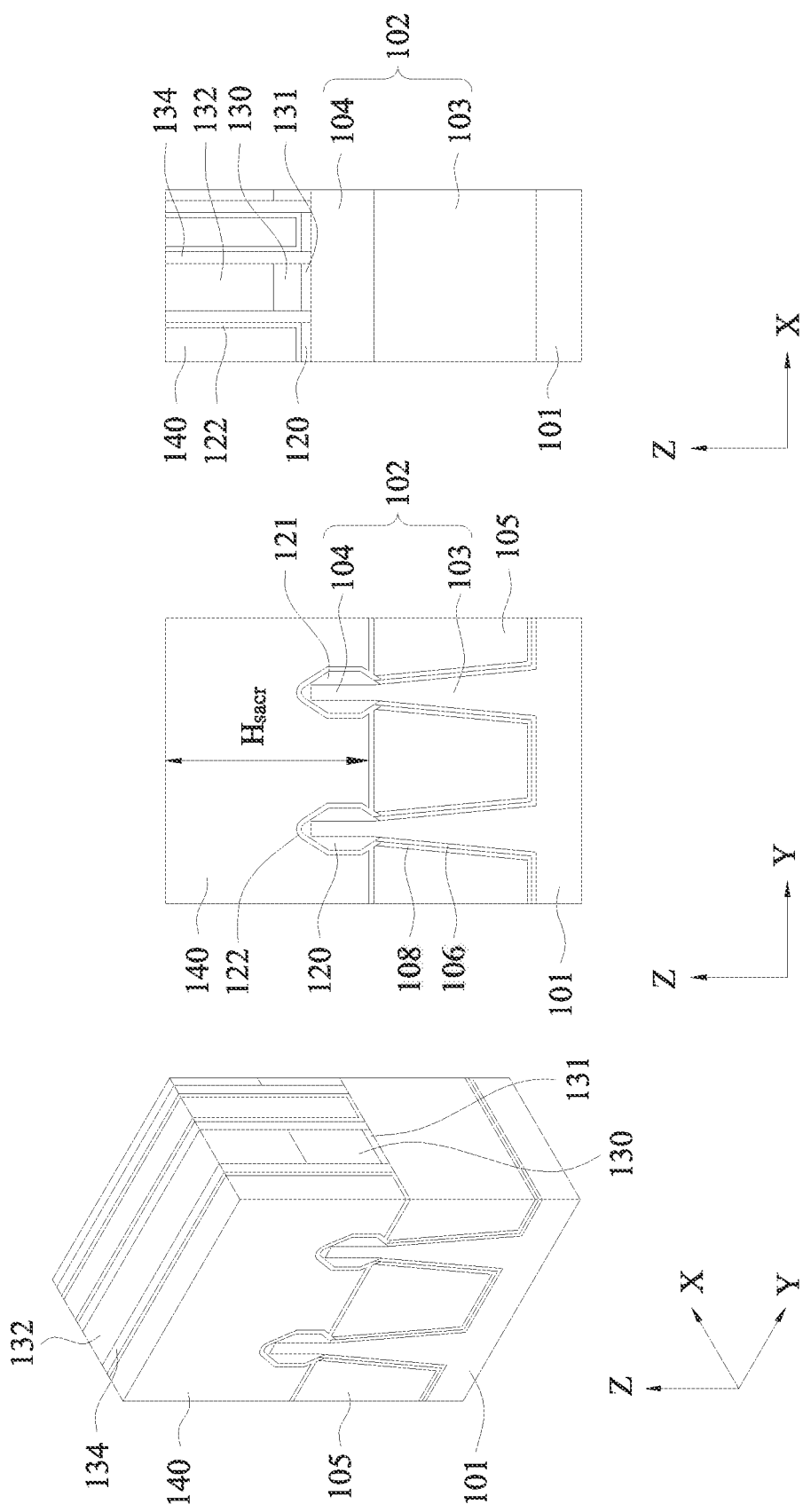

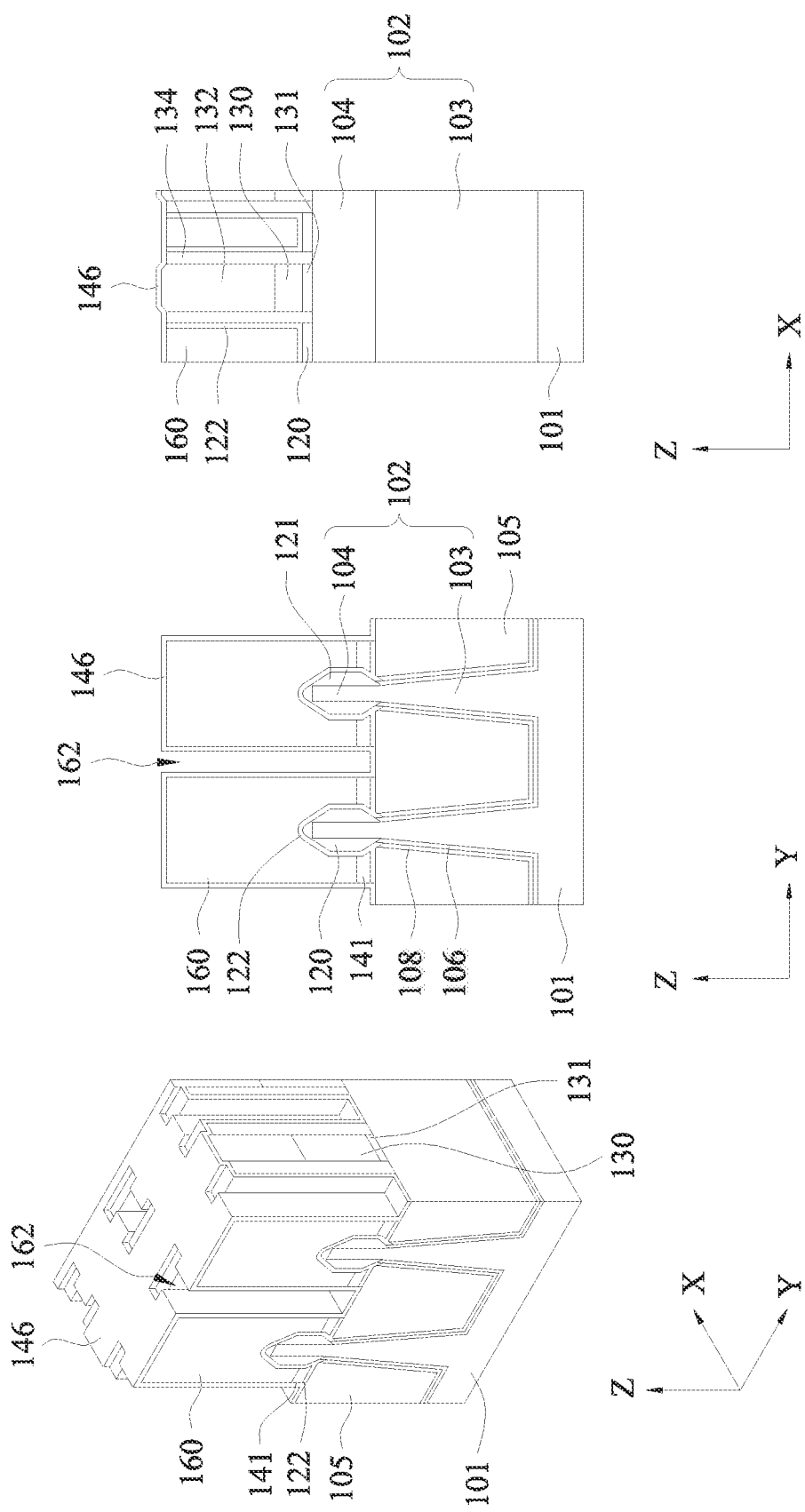

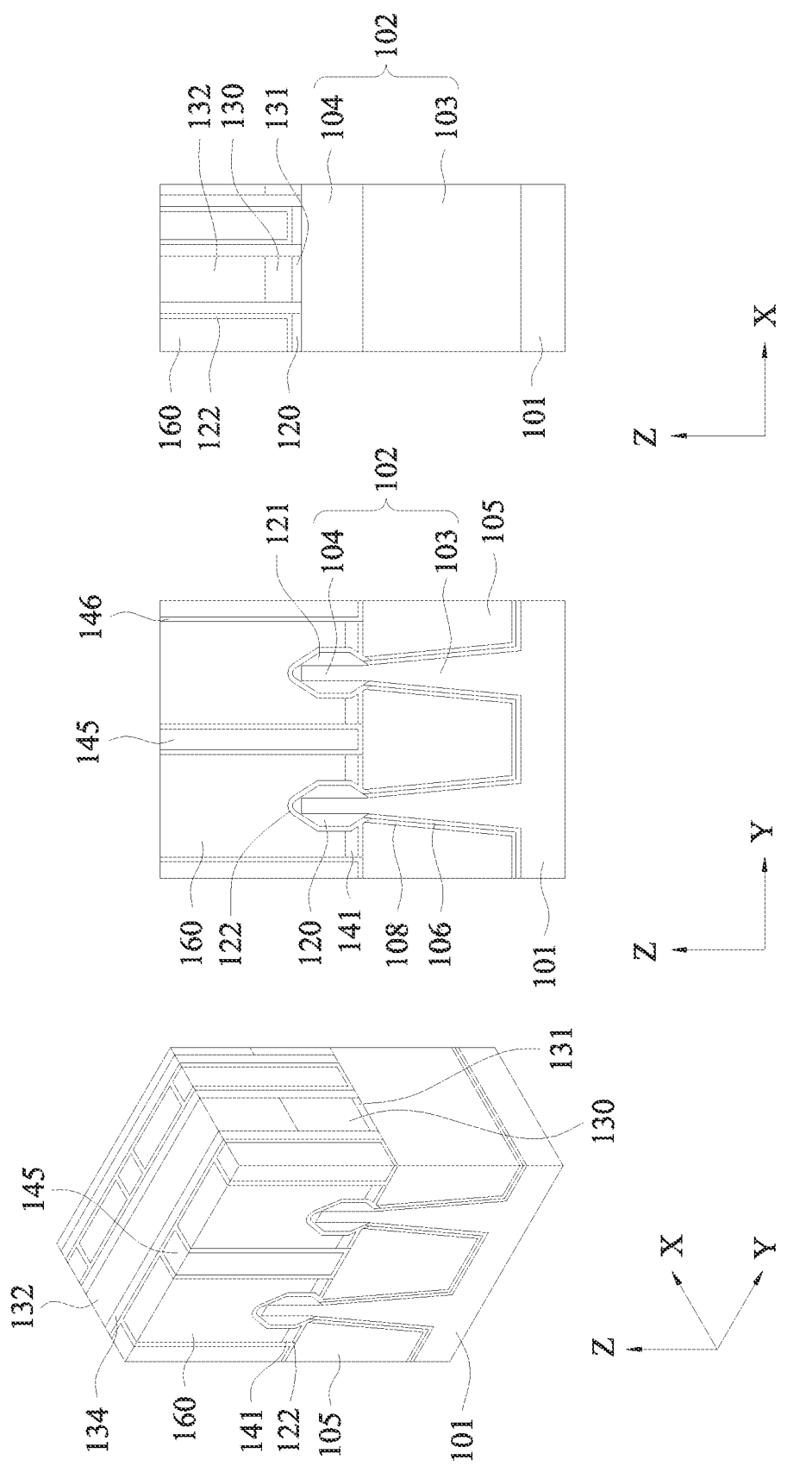

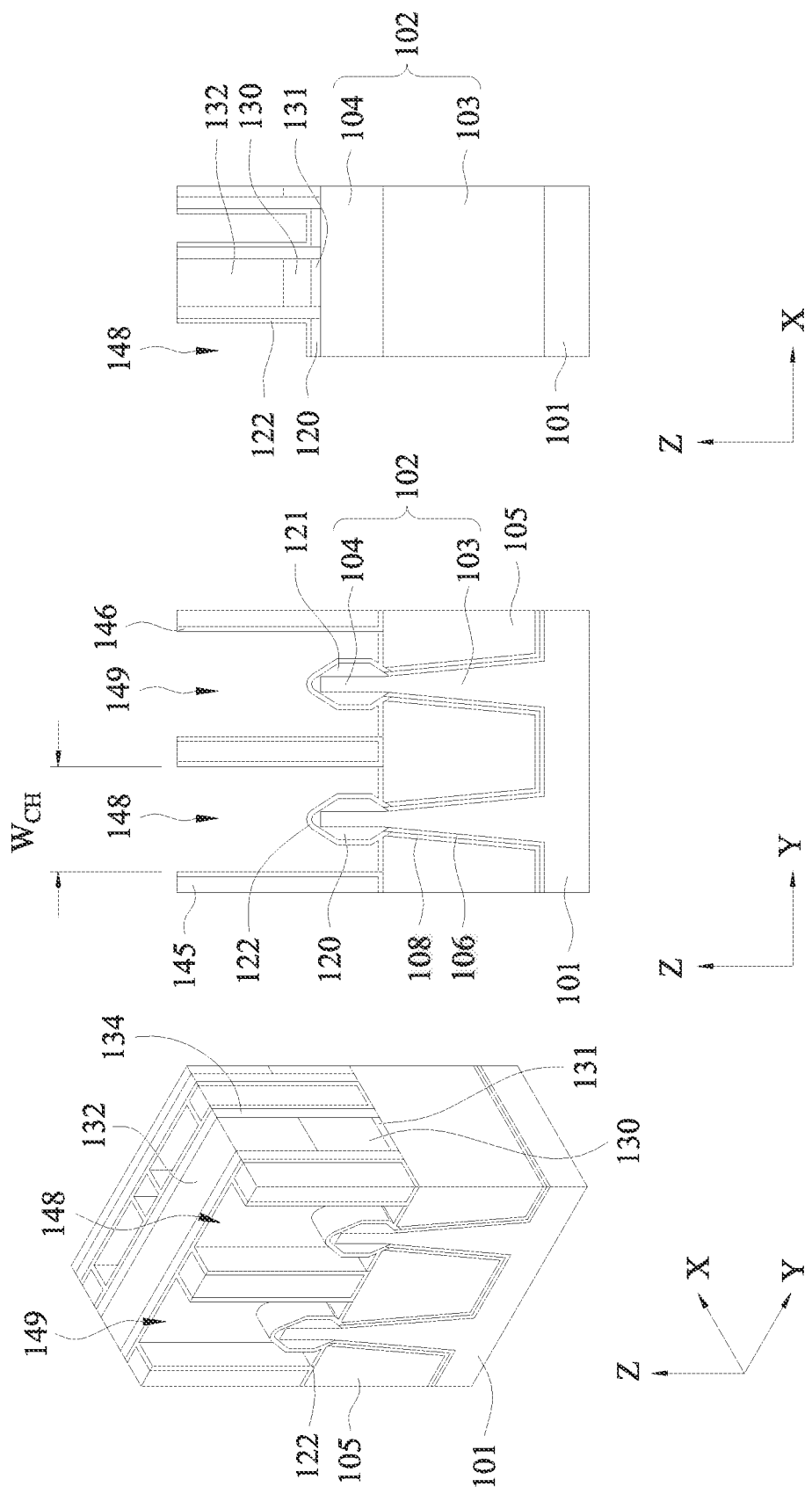

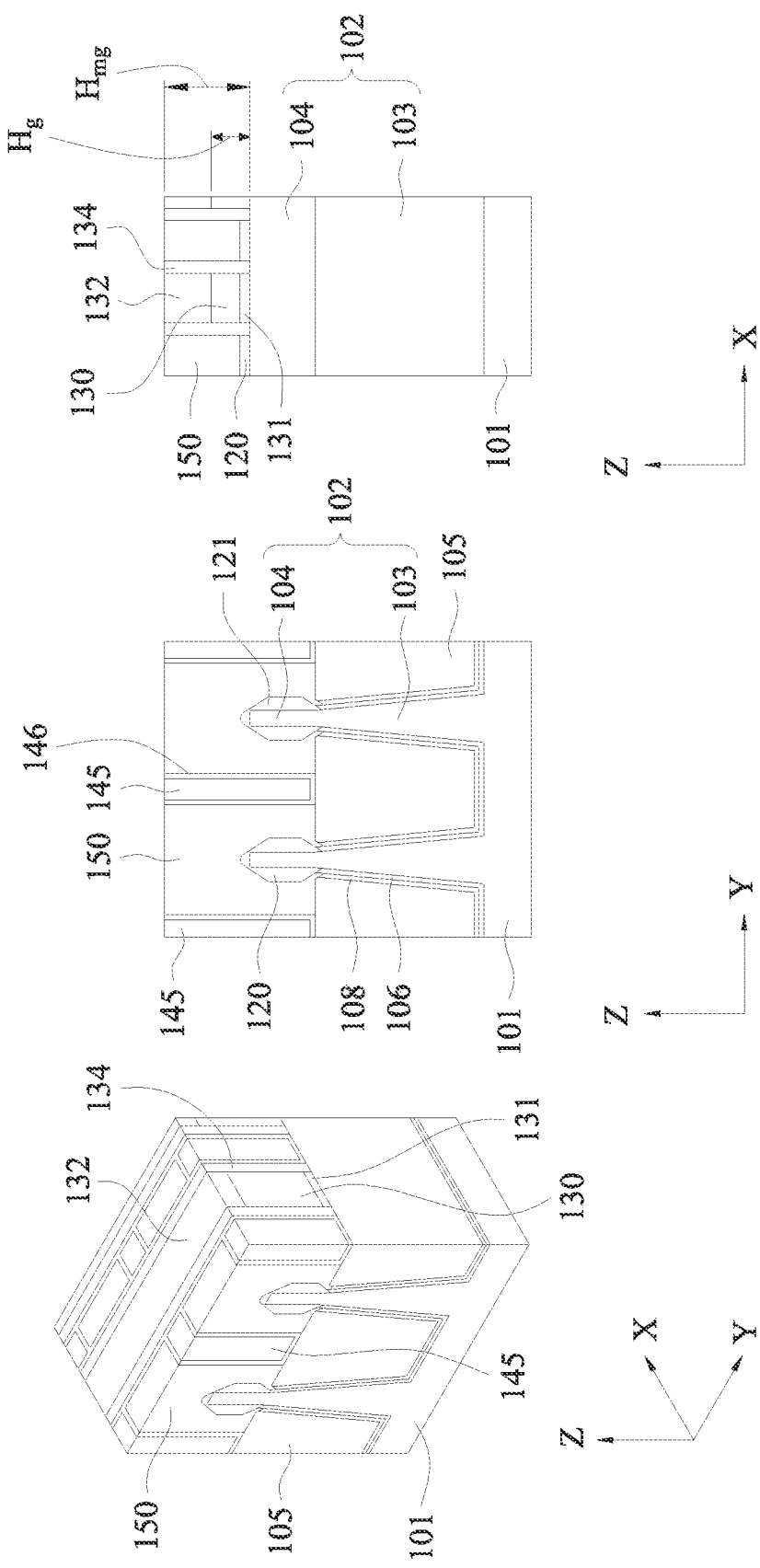

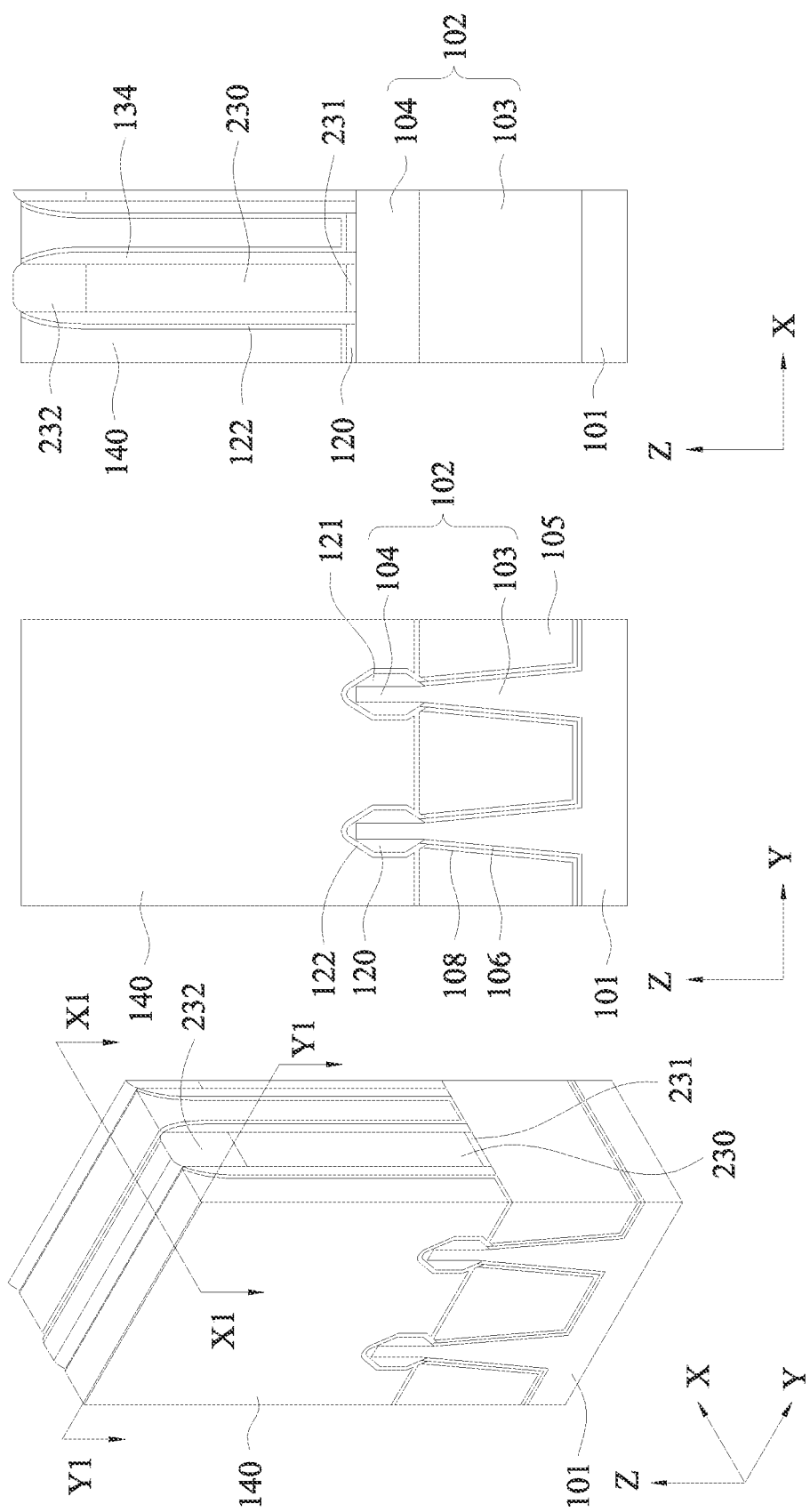

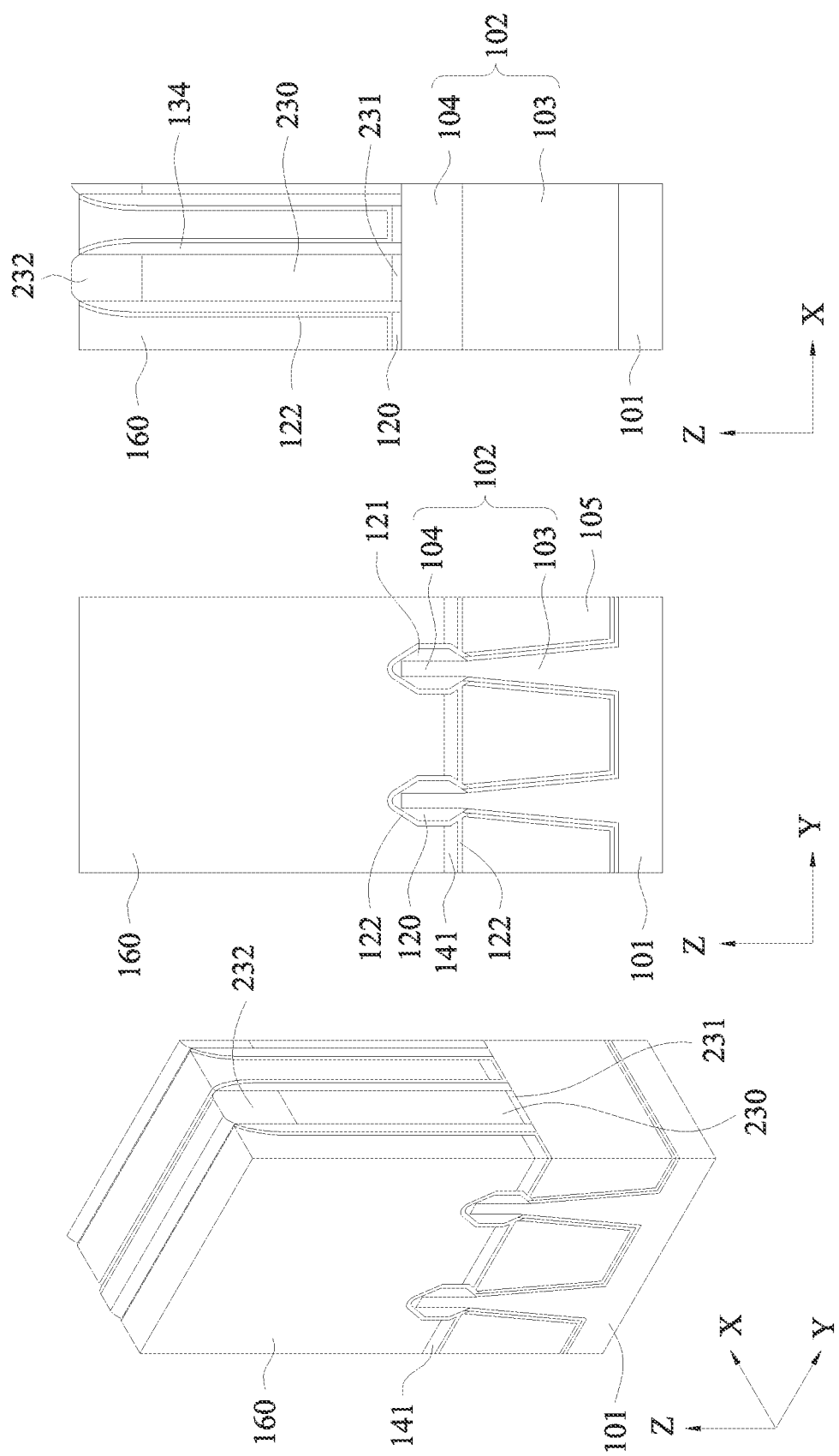

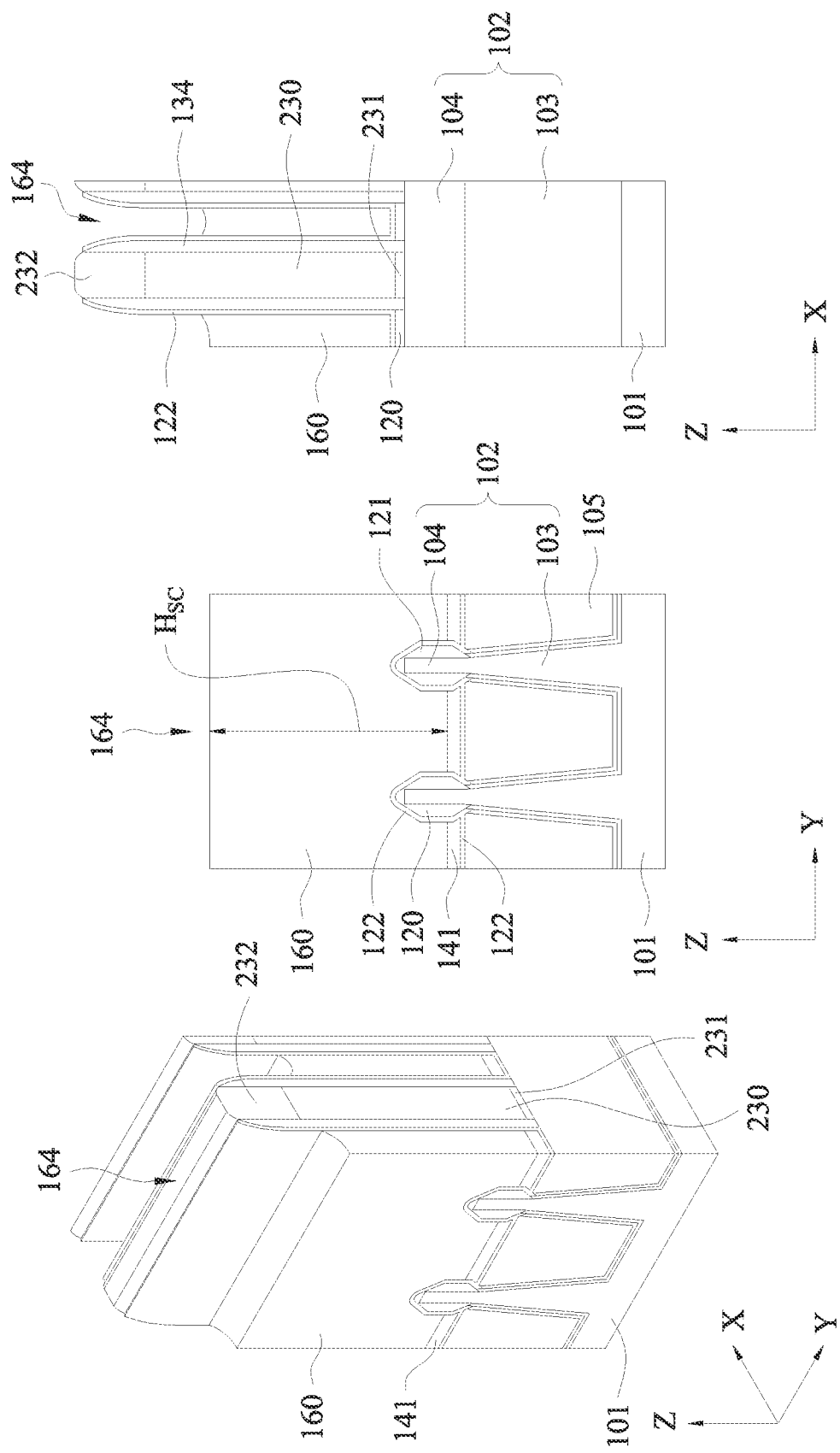

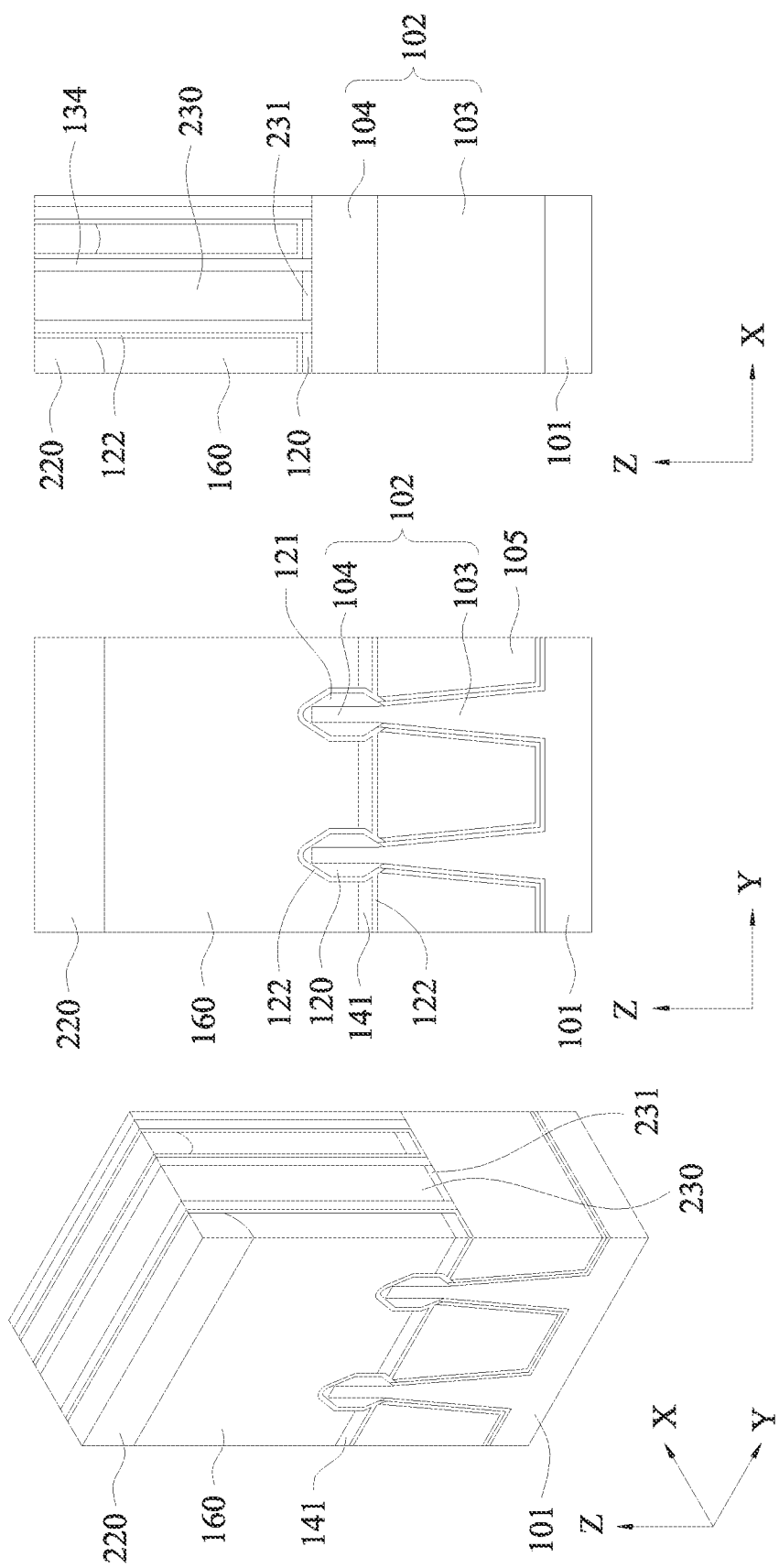

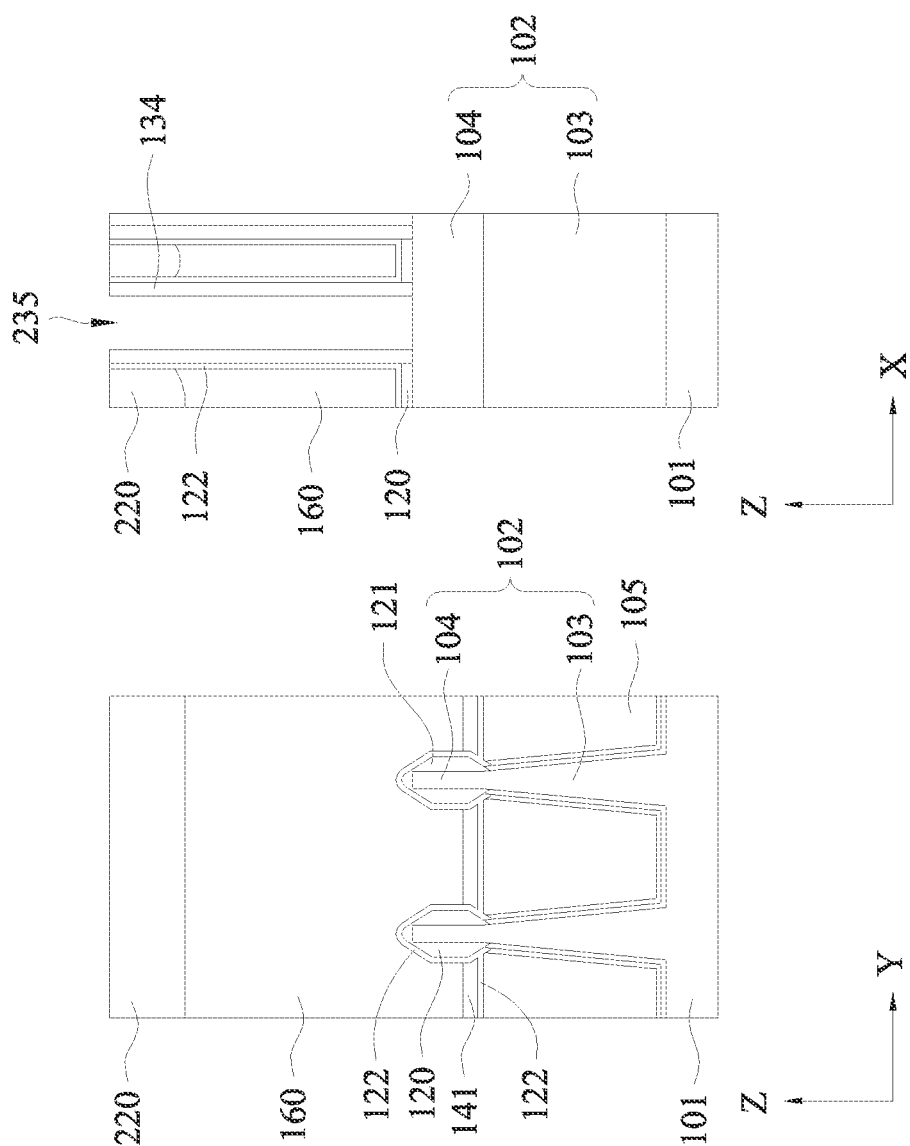
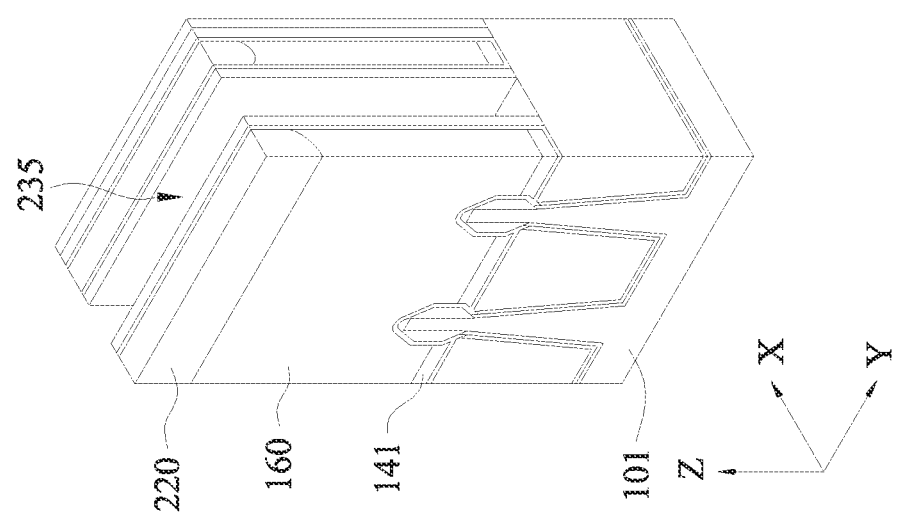
FIG. 17A    FIG. 17B    FIG. 17C

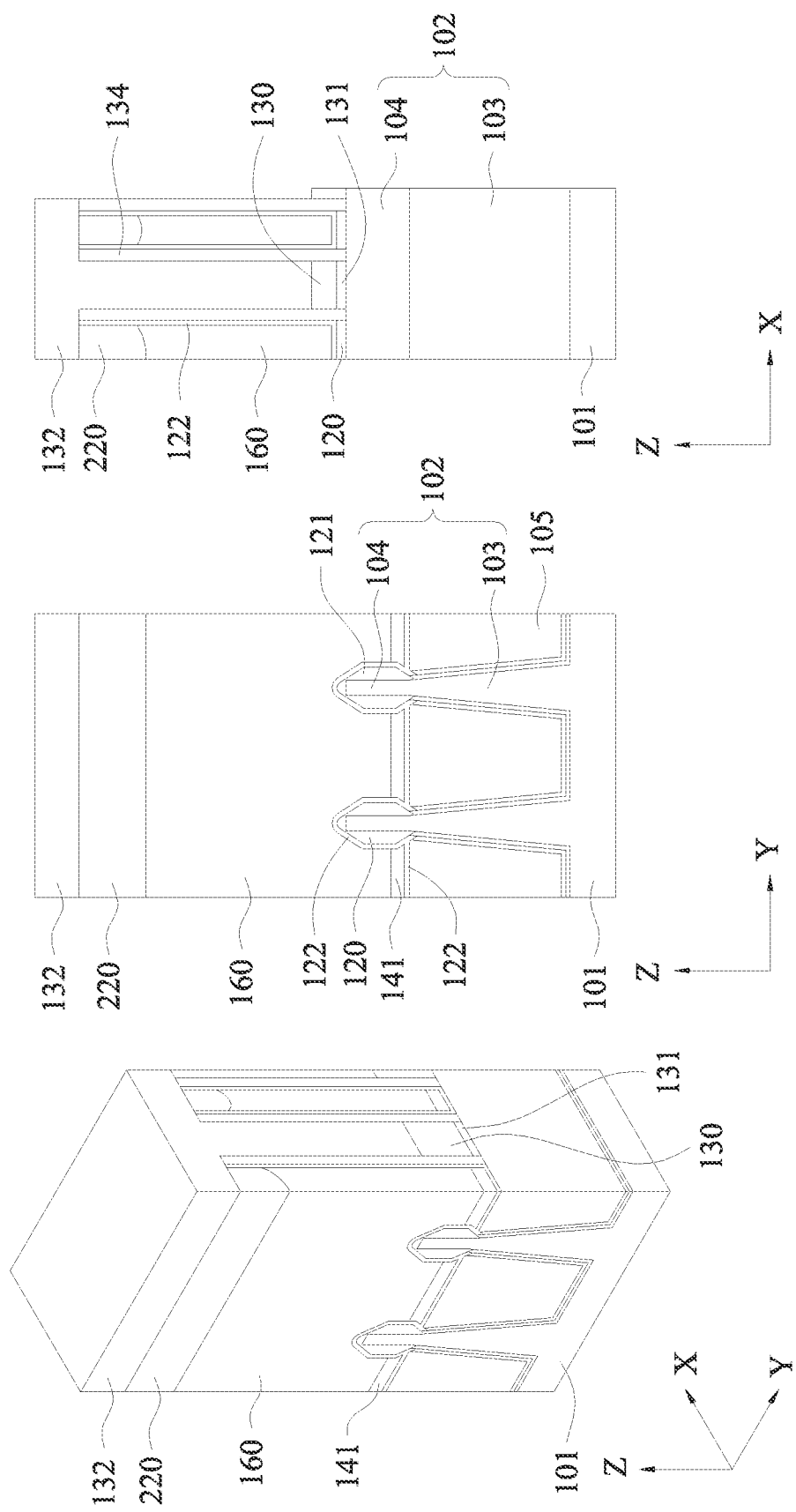

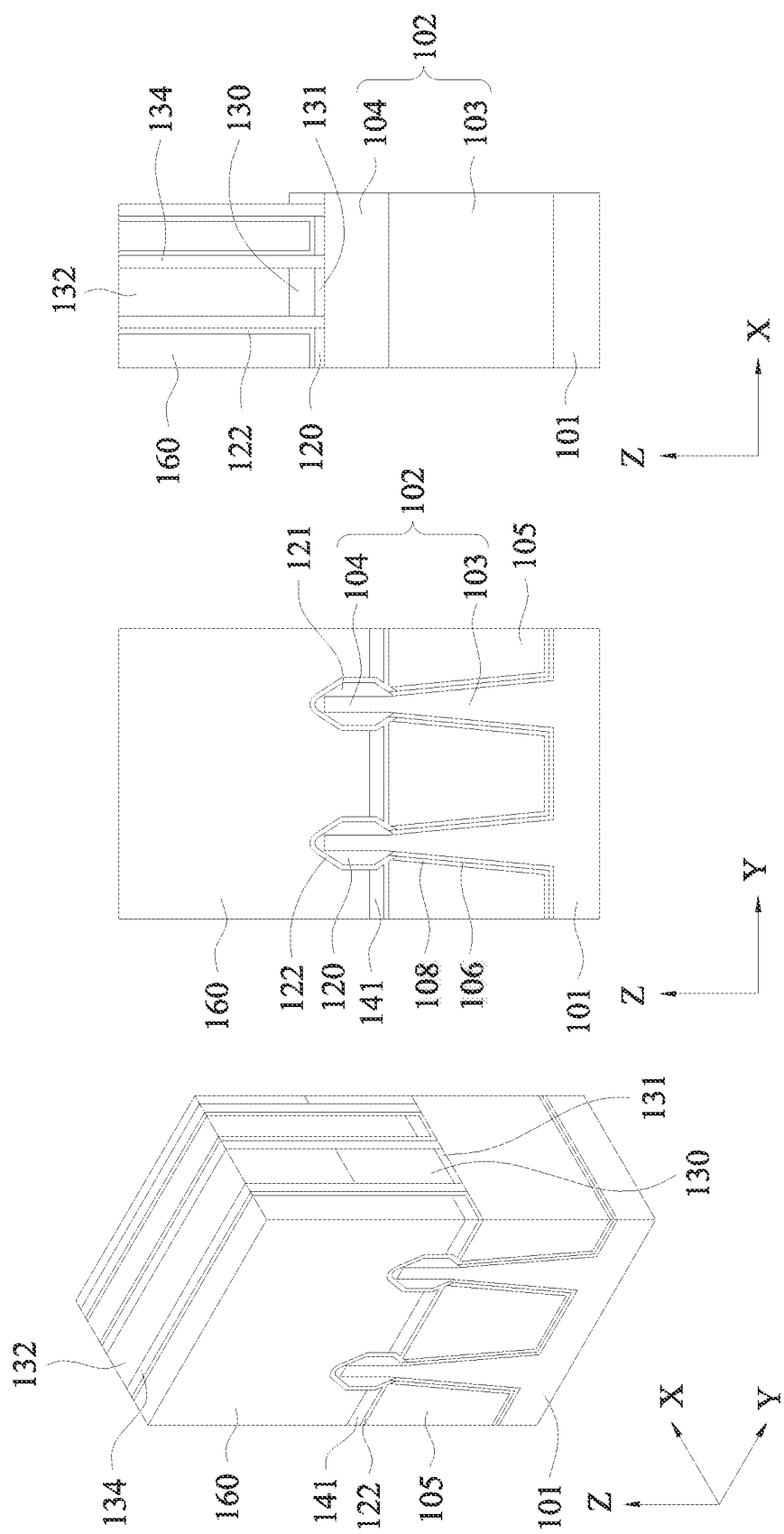

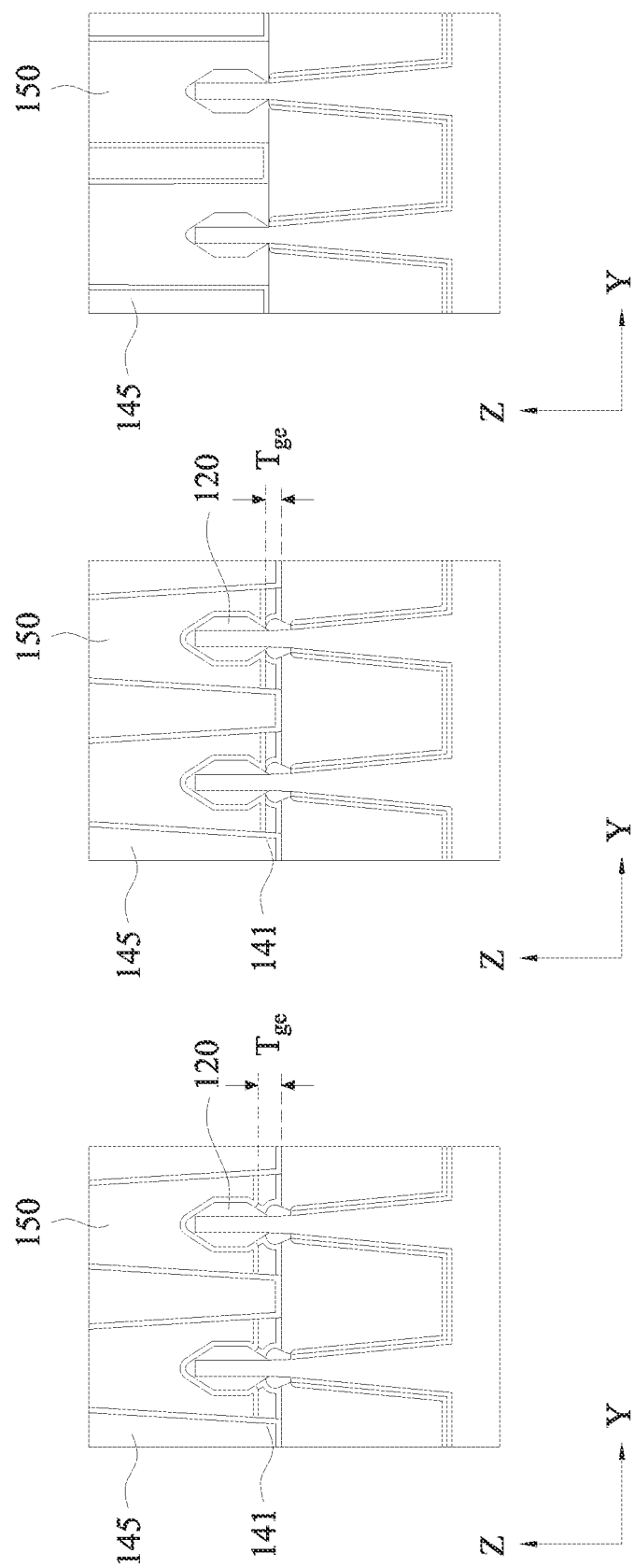

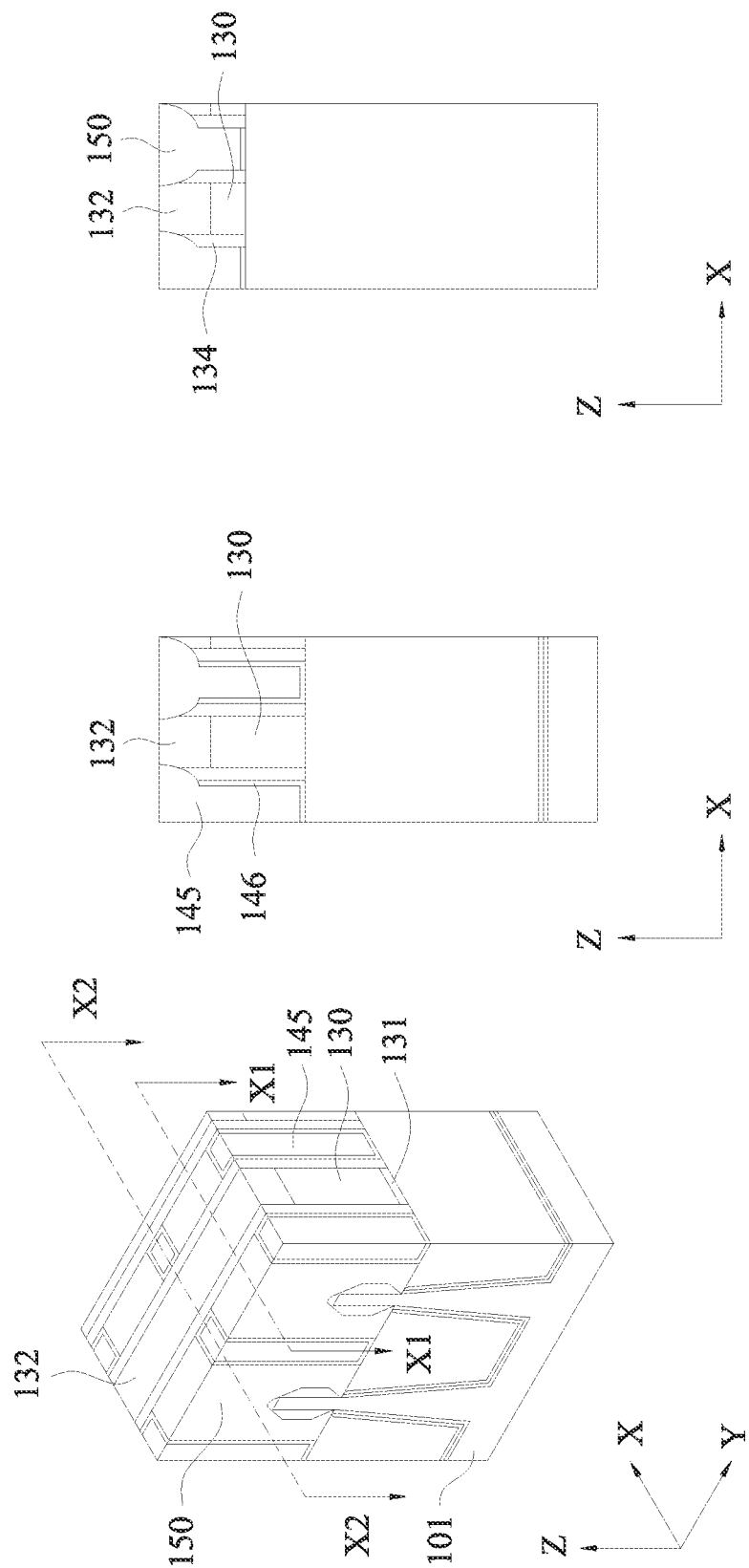

METHOD OF MANUFACTURING A SEMICONDUCTOR DEVICE AND A SEMICONDUCTOR DEVICE

CROSS-REFERENCE TO RELATED APPLICATIONS

This application is a Division of U.S. patent application Ser. No. 17/322,717 filed May 17, 2021, which is a Continuation of U.S. patent application Ser. No. 15/988,624 filed May 24, 2018, now U.S. patent Ser. No. 11/007,005, which is a Division of U.S. patent application Ser. No. 15/602,807 filed May 23, 2017, now U.S. Pat. No. 10,008,497, which claims priority to U.S. Provisional Patent Application 62/427,705 filed Nov. 29, 2016, the entire disclosure each of which is incorporated herein by reference.

TECHNICAL FIELD

The disclosure relates to method of manufacturing semiconductor integrated circuits, and more particularly to method of manufacturing semiconductor devices including fin field effect transistors (FinFETs), and semiconductor devices.

BACKGROUND

As the semiconductor industry has progressed into nanometer technology process nodes in pursuit of higher device density, higher performance, and lower costs, challenges from both fabrication and design issues have resulted in the development of three-dimensional designs, such as a fin field effect transistor (Fin FET) and the use of a metal gate structure with a high-k (dielectric constant) material. The metal gate structure is often manufactured by using gate replacement technologies, and sources and drains are formed by using an epitaxial growth method.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIGS. 1A-1C illustrate one of the various stages in a semiconductor device fabrication process in accordance with embodiments of the present disclosure.

FIGS. 2A-2C illustrate one of the various stages in a semiconductor device fabrication process in accordance with embodiments of the present disclosure.

FIGS. 3A-3C illustrate one of the various stages in a semiconductor device fabrication process in accordance with embodiments of the present disclosure.

FIGS. 7A-7C illustrate one of the various stages in a semiconductor device fabrication process in accordance with embodiments of the present disclosure.

FIGS. 8A-8C illustrate one of the various stages in a semiconductor device fabrication process in accordance with embodiments of the present disclosure.

FIGS. 9A-9C illustrate one of the various stages in a semiconductor device fabrication process in accordance with embodiments of the present disclosure.

FIGS. 10A-10C illustrate one of the various stages in a semiconductor device fabrication process in accordance with embodiments of the present disclosure.

FIGS. 12A-12C illustrate one of the various stages in a semiconductor device fabrication process in accordance with other embodiments of the present disclosure.

FIGS. 14A-14C illustrate one of the various stages in a semiconductor device fabrication process in accordance with other embodiments of the present disclosure.

FIGS. 15A-15C illustrate one of the various stages in a semiconductor device fabrication process in accordance with other embodiments of the present disclosure.

FIGS. 16A-16C illustrate one of the various stages in a semiconductor device fabrication process in accordance with other embodiments of the present disclosure.

FIGS. 17A-17C illustrate one of the various stages in a semiconductor device fabrication process in accordance with other embodiments of the present disclosure.

FIGS. 20A-20C illustrate one of the various stages in a semiconductor device fabrication process in accordance with other embodiments of the present disclosure.

FIGS. 21A-21C illustrate one of the various stages in a semiconductor device fabrication process in accordance with other embodiments of the present disclosure.

FIGS. 24A-24C illustrate views of a semiconductor device in accordance with some embodiments of the present disclosure.

FIGS. 25A-25C illustrate views of a semiconductor device in accordance with some embodiments of the present disclosure.

DETAILED DESCRIPTION

Figures 4A, 4B, 4C:
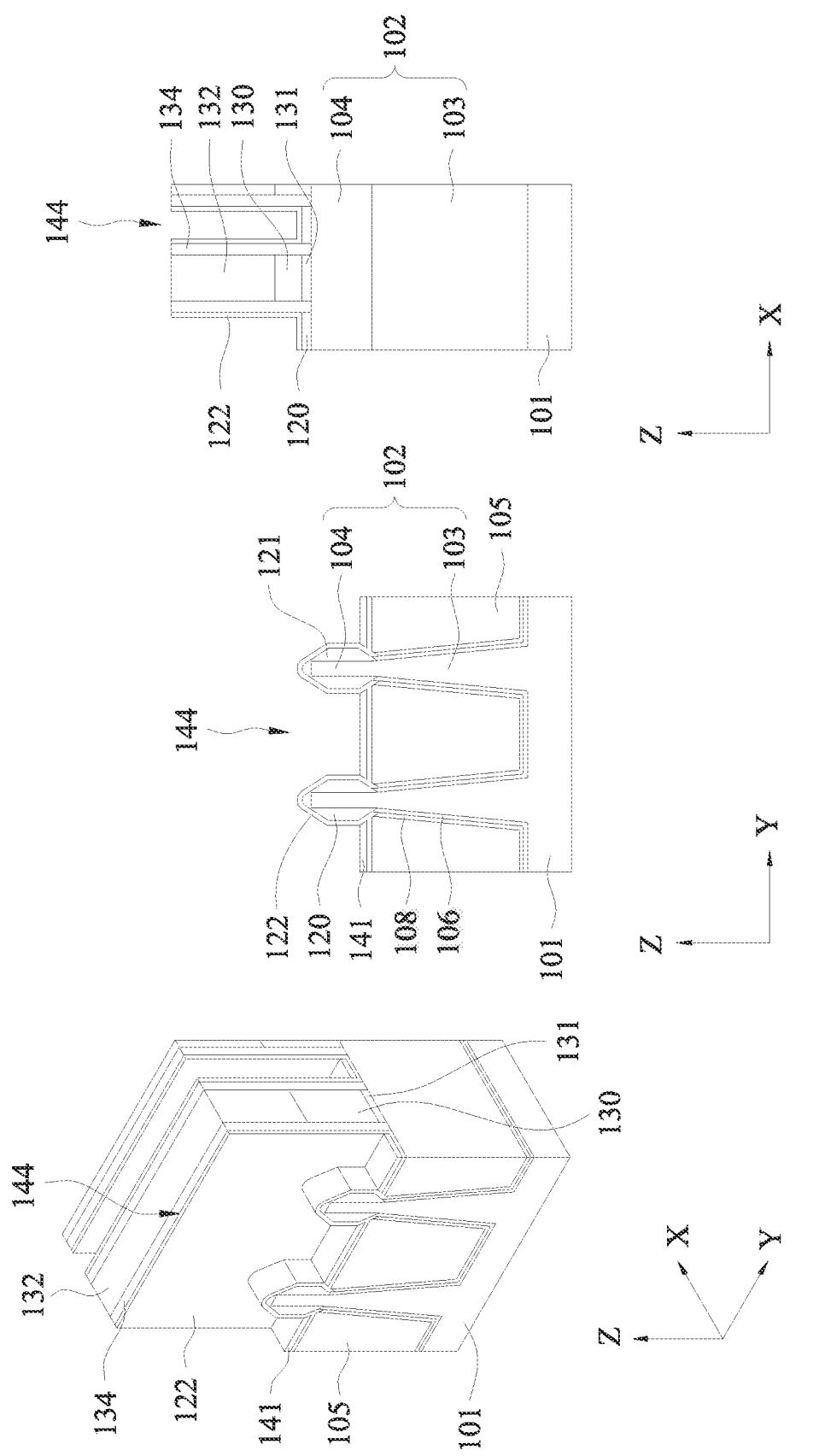
FIGS. 4A-4C illustrate one of the various stages in a semiconductor device fabrication process in accordance with embodiments of the present disclosure.

It is to be understood that the following disclosure provides many different embodiments, or examples, for implementing different features of the invention. Specific embodiments or examples of components and arrangements are described below to simplify the present disclosure. These are, of course, merely examples and are not intended to be limiting. For example, dimensions of elements are not limited to the disclosed range or values, but may depend upon process conditions and/or desired properties of the device. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Various features may be arbitrarily drawn in different scales for simplicity and clarity. In the accompanied drawings, some layers/features may be omitted for simplification.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The device may be otherwise oriented (rotated 90 degrees or at other orientations) and the spatially relative descriptors used herein may likewise be interpreted accordingly. In addition, the term "made of" may mean either "comprising" or "consisting of." Further, in the following fabrication process, there may be one or more additional operations in/between the described operations, and the order of operations may be changed.

Disclosed embodiments relate to a method of forming source/drain (S/D) structures for fin field-effect transistors (FinFETs), a method of patterning openings for the contact over the S/D structures. The embodiments such as those disclosed herein are generally applicable not only to FinFETs but also to double-gate, surround-gate, omega-gate or gate-all-around transistors, 2-dimensional FET and/or nanowire transistors, or any suitable device having a source/drain epitaxial growth process.

FIGS. 1A-10C illustrate various processes in a semiconductor device fabrication process in accordance with some embodiments of the present disclosure. Throughout the various views and illustrative embodiments, like reference numbers are used to designate like elements. In FIGS. 1A-9C, the "A" figures (e.g., FIGS. 1A, 2A, etc.) illustrate a perspective view, the "B" figures (e.g., FIGS. 1B, 2B, etc.) illustrate a cross-sectional view along the Y direction corresponding to line Y1-Y1 illustrated in FIG. 1A, and the "C" figures (e.g., FIG. 1C, 2C, etc.) illustrate a cross-sectional view along the X direction corresponding to line X1-X1 illustrated in in FIG. 1A. It is understood that additional operations can be provided before, during, and after processes shown by FIGS. 1A-10C, and some of the operations described below can be replaced or eliminated, for additional embodiments of the method. The order of the operations/processes may be interchangeable.

Referring first to FIGS. 1A-1C, FIGS. 1A-1C illustrate the structure after various manufacturing operations to form a FinFET structure are performed. As shown in FIGS. 1A-1C, source/drain (S/D) structures 120 and 121 and a metal gate 130 together with gate dielectric layer 131 are formed over a substrate 101. In some embodiments, the S/D structure 120 is for a p-channel FET and the S/D structure 121 is for an n-channel FET (i.e., different conductivity types). In other embodiments, both the S/D structures 120, 121 are for p-channel FETs or for n-channel FETs (i.e., the same conductivity type). This structure may be formed by the following manufacturing operations.

In FIGS. 1A-1C, there is shown a substrate 101 having one or more fin structures, with two fin structures 102 being illustrated. It is understood that two fin structures are illustrated for purposes of illustration, but other embodiments may include any number of fin structures. In some embodiments, one or more dummy fin structures are formed adjacent to the fin structure for an active FinFET. The fin structure 102 extends in the X direction and protrudes from the substrate in the Z direction, while the gate 130 extends in the Y direction.

The substrate 101 may comprise various doped regions depending on design requirements (e.g., p-type substrate or n-type substrate). In some embodiments, the doped regions may be doped with p-type or n-type dopants. For example, the doped regions may be doped with p-type dopants, such as boron or $BF_2$; n-type dopants, such as phosphorus or arsenic; and/or combinations thereof. The doped regions may be configured for an n-type FinFET, or alternatively configured for a p-type FinFET.

In some embodiments, the substrate 101 may be made of a suitable elemental semiconductor, such as silicon, diamond or germanium; a suitable alloy or compound semiconductor, such as Group-IV compound semiconductors (silicon germanium (SiGe), silicon carbide (SiC), silicon germanium carbide (SiGeC), GeSn, SiSn, SiGeSn), Group III-V compound semiconductors (e.g., gallium arsenide, indium gallium arsenide InGaAs, indium arsenide, indium phosphide, indium antimonide, gallium arsenic phosphide, or gallium indium phosphide), or the like. Further, the substrate 101 may include an epitaxial layer (epi-layer), which may be strained for performance enhancement, and/or may include a silicon-on-insulator (SOI) structure.

The fin structure 102 may be formed using, for example, a patterning process to form trenches such that a trench is formed between adjacent fin structures 102. As discussed in greater detail below, the fin structure 102 will be used to form a FinFET.

Isolation regions, such as shallow trench isolations (STI) 105, are disposed in the trenches over the substrate 101. Prior to forming the isolation insulating layer 105, one or more liner layers are formed over the substrate 101 and sidewalls of the bottom part 103 of the fin structures 102 in some embodiments. In some embodiments, the liner layers includes a first fin liner layer 106 formed on the substrate 101 and sidewalls of the bottom part 103 of the fin structures 102, and a second fin liner layer 108 formed on the first fin liner layer 106. Each of the liner layers has a thickness between about 1 nm and about 20 nm in some embodiments.

In some embodiments, the first fin liner layer 106 includes silicon oxide and has a thickness between about 0.5 nm and about 5 nm, and the second fin liner layer 108 includes silicon nitride and has a thickness between about 0.5 nm and about 5 nm. The liner layers may be deposited through one or more processes such as physical vapor deposition (PVD), chemical vapor deposition (CVD), or atomic layer deposition (ALD), although any acceptable process may be utilized.

The isolation insulating layer 105 may be made of suitable dielectric materials such as silicon oxide, silicon nitride, silicon oxynitride, fluorine-doped silicate glass (FSG), low-k dielectrics such as carbon doped oxides, extremely low-k dielectrics such as porous carbon doped silicon dioxide, a polymer such as polyimide, combinations of these, or the like. In some embodiments, the isolation insulating layer 105 is formed through a process such as CVD, flowable CVD (FCVD), or a spin-on-glass process, although any acceptable process may be utilized. Subsequently, portions of the isolation insulating layer 105 extending over the top surfaces of the fin structures 102, and portions of the liner layers over the top surfaces of the fin structures 102 are removed using, for example, an etch process, chemical mechanical polishing (CMP), or the like.

In some embodiments, the isolation insulating layer 105 and the liner layers are recessed to expose the upper portion 104 of the fin structure 102 as illustrated in FIGS. 1A-1C. In some embodiments, the isolation insulating layer 105 and the liner layers are recessed using a single etch processes, or multiple etch processes. In some embodiments in which the isolation insulating layer 105 is made of silicon oxide, the etch process may be, for example, a dry etch, a chemical etch, or a wet cleaning process. For example, the chemical etch may employ fluorine-containing chemical such as dilute hydrofluoric (dHF) acid. After the fin formation process, the fin height $H_{fin}$ is about 30 nm or higher, such as about 50 nm or higher, in some embodiments. In one embodiment, the fin height is between about 40 nm and about 80 nm. It is understood that the fin height may be modified by subsequent processing. Other materials, processes, and dimensions may be used.

After the fin structure 102 is formed, a dummy gate structure including a dummy gate dielectric layer and a dummy gate electrode are formed over the exposed fin structure 102. The dummy gate dielectric layer and the dummy gate electrode will be subsequently used to define and form the source/drain regions. In some embodiments, the dummy gate dielectric layer and the dummy gate electrode are formed by depositing and patterning a dummy dielectric layer formed over the exposed fin structures 102 and a dummy electrode layer over the dummy gate dielectric layer. The dummy dielectric layer may be formed by thermal oxidation, CVD, sputtering, or any other methods known and used in the art for forming a dummy dielectric layer. In some embodiments, the dummy dielectric layer may be made of one or more suitable dielectric materials such as silicon oxide, silicon nitride, SiCN, SiON, and SiN, low-k dielectrics such as carbon doped oxides, extremely low-k dielectrics such as porous carbon doped silicon dioxide, a polymer such as polyimide, the like, or a combination thereof. In one embodiment, $SiO_2$ is used.

Subsequently, the dummy electrode layer is formed over the dummy dielectric layer. In some embodiments, the dummy electrode layer is a conductive material and may be selected from a group comprising amorphous silicon, poly silicon, amorphous germanium, poly germanium, amorphous silicon-germanium, poly silicon-germanium, metallic nitrides, metallic silicides, metallic oxides, and metals. The dummy electrode layer may be deposited by PVD, CVD, sputter deposition, or other techniques known and used in the art for depositing conductive materials. Other materials, conductive and non-conductive, may be used. In one embodiment, poly-Si is used.

A mask pattern may be formed over the dummy electrode layer to aid in the patterning. The mask pattern is made of one or more layers of $SiO_2$, SiCN, SiON, $Al_2O_3$, SiN, or other suitable materials. By using the mask pattern as an etching mask, the dummy electrode layer is patterned into the dummy gate electrode. In some embodiments, the dummy dielectric layer is also patterned to define the dummy gate dielectric layer.

Subsequently, sidewall spacers 134 are formed along sidewalls of the dummy gate structure. The sidewall spacers 134 may be formed by depositing and anisotropically etching an insulating layer deposited over the dummy gate structure, the fin structure 102, and the isolation insulating layer 105. In some embodiments, the sidewall spacers 134 are formed of silicon nitride, and may have a single-layer structure. In alternative embodiments, the sidewall spacers 134 may have a composite structure including a plurality of layers. For example, the sidewall spacers 134 may include a silicon oxide layer and a silicon nitride layer over the silicon oxide layer. Other materials, such as $SiO_2$, SiCN, SiON, SiN, SiOCN, other low k material, or combinations thereof, may also be used. The thickness of the sidewall spacer 134 is in a range from about 5 nm to about 40 nm in some embodiments.

After the dummy gate structure and the sidewall spacers are formed, source/drain (S/D) structures 120 and 121 are formed on exposed portions 104 of the fin structures 102 along opposing sides of the dummy gate structure. The S/D structures 120 and 121 may be epitaxially formed on the side faces and the top face of the exposed fin structure 104. In some embodiments, the fin structure 104 may be recessed and the S/D structure is epitaxially formed on the exposed portion of the recessed fin. The use of epitaxial grown materials in the source/drain regions allows for the source/drain regions to exert stress in a channel of a FinFET. When the S/D structures 120 and 121 are for different conductivity type FETs, the S/D structure 120 is formed while the fin structure for the S/D structure 121 is covered by a protective layer made of, for example, SiN, and then the S/D structure 121 is formed while the formed S/D structure 120 is covered by a protective layer.

The materials used for the S/D structures 120 and 121 may be varied for the n-type and p-type FinFETs, such that one type of material is used for the n-type FinFETs to exert a tensile stress in the channel region and another type of material for the p-type FinFETs to exert a compressive stress. For example, SiP or SiC may be used to form n-type FinFETs, and SiGe or Ge may be used to form p-type FinFETs. Other materials may be used. In some embodiments, the S/D structures 120 and/or 121 include two or more epitaxial layers with different composition and/or different dopant concentrations.

The S/D structures 120 and/or 121 may be doped either through an implanting process to implant appropriate dopants, or by in-situ doping as the material is grown. For example, for a p-channel FET where the channel may be Si or $Si_{1-x}Ge_x$, the doped epitaxial film may be boron-doped $Si_{1-y}Ge_y$, where y is equal to or larger than x to induce longitudinal compressive strain in the channel for hole mobility enhancement. For an n-channel FET where the channel may be Si, the doped epitaxial film may be, for example, phosphorus-doped silicon (Si:P) or silicon-carbon ($Si_{1-z}C_z$:P). In the case where the channel is a compound semiconductor such as $In_mGa_{1-m}As$, the doped epitaxial film may be, for example, $In_nGa_{1-n}As$, where n is smaller than or equal to m.

As shown in FIGS. 1A and 1B, in some embodiments, the cross section of the S/D structures 120 and/or 121 in the Y direction have substantially a hexagonal shape, and in other embodiments, the cross section of the S/D structures 120 and/or 121 has a diamond shape, a pillar shape or a bar shape. The width $W_{SD}$ of the S/D structure in the Y direction is in a range from about 25 nm to about 100 nm in some embodiments.

After the S/D structures 120 and 121 are formed, a first insulating layer 122 as a liner layer or a contact etch stop layer (CESL) is deposited to cover the S/D structures 120 and 121 and on the sidewalls spacers 134 of the dummy gate structure. The first insulating layer 122 acts as an etch stop during the patterning of a subsequently formed dielectric material. In some embodiments, the first insulating layer 122 includes $SiO_2$, SiCN, SiON, SiN and other suitable dielectric materials. In one embodiment, SiN is used. The first insulating layer 122 may be made of a plurality of layers that comprises combinations of the above mentioned materials. The first insulating layer 122 may be deposited through one or more processes such as PVD, CVD, or ALD, although any acceptable process may be utilized. Other materials and/or processes may be used. In some embodiments, the first insulating layer 122 has a thickness between about 0.5 nm and about 10 nm. Other thicknesses may be used in other embodiments.

After the first insulating layer 122 is formed, a first sacrificial layer 115 is formed over the first insulating layer 122. In some embodiments, the first sacrificial layer includes one or more layers of silicon based dielectric material, such as $SiO_2$, SiCN, SiON, SiOC, SiOH, SiN, or other suitable dielectric materials. In some embodiments, the first sacrificial layer 115 is formed through a film forming process, such as, CVD, PVD, ALD, FCVD, or a spin-on-glass process, although any acceptable process may be utilized. Subsequently, portions of the first insulating layer 122 are removed using, for example, an etch process, CMP, or the like, to exposed the upper surface of the dummy gate electrode.

Subsequently, the dummy gate electrode and the dummy gate dielectric layer are removed. The removal process may include one or more etch processes. For example in some embodiments, the removal process includes selectively etching using either dry or wet etching. When dry etching is used, the process gas may include $CF_4$, $CHF_3$, $NF_3$, $SF_6$, $Br_2$, HBr, $Cl_2$, or combinations thereof. Diluting gases such as $N_2$, $O_2$, or Ar may optionally be used. When wet etching is used, the etching solution (etchant) may include $NH_4OH$:$H_2O_2$:$H_2O$ (APM), $NH_2OH$, KOH, $HNO_3$:$NH_4F$:$H_2O$, and/or the like. The dummy gate dielectric layer may be removed using a wet etch process, such as a diluted HF acid. Other processes and materials may be used.

After the dummy gate structure is removed, a gate dielectric layer 131 is formed over a channel region of the fin structure 104. In some embodiments, the gate dielectric layer 131 includes one or more high-k dielectric layers (e.g., having a dielectric constant greater than 3.9). For example, the one or more gate dielectric layers may include one or more layers of a metal oxide or a silicate of Hf, Al, Zr, combinations thereof, and multi-layers thereof. Other suitable materials include La, Mg, Ba, Ti, Pb, Zr, in the form of metal oxides, metal alloye oxides, and combinations thereof. Exemplary materials include $MgO_x$, $BaTi_xO_y$, $BaSr_xTi_yO_z$, $PbTi_xO_y$, $PbZr_xTi_yO_z$, SiCN, SiON, SiN, $Al_2O_3$, $La_2O_3$, $Ta_2O_3$, $Y_2O_3$, $HfO_2$, $ZrO_2$, HfSiON, $YGe_xO_y$, $YSi_xO_y$, and $LaAlO_3$, and the like. The formation methods of gate dielectric layer 131 include molecular-beam deposition (MBD), ALD, PVD, and the like. In some embodiments, the gate dielectric layer 131 has a thickness of about 0.5 nm to about 5 nm. In some embodiments, the gate dielectric layer 131 is formed also on sides of the sidewall spacers 134.

In some embodiments, an interfacial layer (not shown) is formed over the channel region 104 prior to forming the gate dielectric layer 131, and the gate dielectric layer 131 is formed over the interfacial layer. The interfacial layer helps buffer the subsequently formed high-k dielectric layer from the underlying semiconductor material. In some embodiments, the interfacial layer is a chemical silicon oxide, which may be formed by chemical reactions. For example, a chemical silicon oxide may be formed using deionized water+ozone ($DIO_3$), $NH_4OH$+$H_2O_2$+$H_2O$ (APM), or other methods. Other embodiments utilize a different material or processes for the interfacial layer. In an embodiment, the interfacial layer has a thickness of about 0.2 nm to about 1 nm.

After the gate dielectric layer 131 is formed, a gate electrode 130 is formed over the gate dielectric layer 131. The gate electrode 130 may be a metal selected from a group of W, Cu, Ti, Ag, Al, TiAl, TiAlN, TaC, TaCN, TaSiN, Mn, Co, Pd, Ni, Re, Ir, Ru, Pt, and Zr. In some embodiments, the gate electrode 130 includes a metal selected from a group of TiN, WN, TaN, and Ru. Metal alloys such as Ti—Al, Ru—Ta, Ru—Zr, Pt—Ti, Co—Ni and Ni—Ta may be used and/or metal nitrides such as $WN_x$, $TiN_x$, $MoN_x$, $TaN_x$, and $TaSi_xN_y$ may be used. In some embodiments, the gate electrode 130 has a thickness in the range of about 5 nm to about 100 nm. The gate electrode 130 may be formed using a suitable process such as ALD, CVD, PVD, plating, or combinations thereof. A planarization process, such as a CMP, may be performed to remove excess materials.

In certain embodiments of the present disclosure, the gate electrode 130 includes one or more work function adjustment layers (not shown) disposed on the gate dielectric layer 131. The work function adjustment layer is made of a conductive material such as a single layer of TiN, TaN, TaAlC, TiC, TaC, Co, Al, TiAl, HfTi, TiSi, TaSi or TiAlC, or a multilayer of two or more of these materials. For the n-channel FinFET, one or more of TaN, TaAlC, TiN, TiC, Co, TiAl, HfTi, TiSi and TaSi is used as the work function adjustment layer, and for the p-channel FinFET, one or more of TiAlC, Al, TiAl, TaN, TaAlC, TiN, TiC and Co is used as the work function adjustment layer.

Then, the gate electrode 130, the gate dielectric layer 131 and the work function adjustment layer are recessed, and a gate cap layer 132 is formed on the recessed gate electrode 130. In some embodiments, when the gate electrode 130 is mainly made of W, the gate electrode may be recessed using, for example, dry etch process using $Cl_2$/$O_2$/$BCl_3$, at a temperature range of 24° C. to 150° C., and at a pressure of below 1 Torr.

After recessing the gate electrode 130, the gate cap layer 132 is formed in the recess to protect the gate electrode 130 during subsequent processes. In some embodiments, the gate cap layer 132 includes $SiO_2$, SiCN, SiON, SiN, $Al_2O_3$, $La_2O_3$, SiN, a combination thereof, or the like, but other suitable dielectric films may be used. The gate cap layer 132 may be formed using, for example, CVD, PVD, spin-on, or the like. Other suitable process steps may be used. A planarization process, such as a CMP, may be performed to remove excess materials.

FIGS. 2A-2C show views of one of the various stages for manufacturing a FinFET device according to some embodiments of the present disclosure.

As shown in FIGS. 2A-2C, the first sacrificial layer 115 is at least partially removed from both side regions of the S/D structures 120 and 121, to form openings 116. In some embodiments, all of the first sacrificial layer 115 is removed. The first sacrificial layer 115 may be removed by suitable etching operations, such as dry etching and/or wet etching. The etching operation substantially stops at the first insulating layer 122. In some embodiments, the first insulating layer 122 has a thickness between about 0.5 nm and about 10 nm.

FIGS. 3A-3C show views of one of the various stages for manufacturing a FinFET device according to some embodiments of the present disclosure.

After the openings 116 are formed, a second sacrificial layer 140 is formed in the openings 116. The second sacrificial layer 140 is made of a material having a higher (e.g., 5 or more) etching selectivity with respect to the materials of the first insulating layer 122 and/or the isolation insulating layer 105. In some embodiments, the second sacrificial layer 140 is made of one or more layers of Group IV elemental or compound materials, such as Si, SiGe, SiC, Ge, SiGeC and GeSn, which may be crystalline, polycrystalline or amorphous and may be doped or un-doped. In other embodiments, the second sacrificial layer 140 is made of one or more silicon based dielectric layers of SiOC, SiC, SiON, SiCN, SiOCN, SiN and/or $SiO_2$. Aluminum based dielectric materials, such as aluminum oxide, aluminum oxy-carbide and aluminum oxy-nitride may be used. A SOC (spin-on-carbon) may also be used. In certain embodiments, the second sacrificial layer 140 is made of one or more layers of Group III-V compound semiconductor including, but not limited to, GaAs, GaN, InGaAs, InAs, InP, InSb, InAsSb, AlN and/or AlGaN. The second sacrificial layer 140 may be deposited through one or more processes such as PVD, CVD, or ALD, although any acceptable process may be utilized. Other materials and/or processes may be used. In one embodiment, amorphous or poly Si is used as the second sacrificial layer 140. In other embodiments, amorphous or poly $Si_{1-x}Ge_x$, where x is equal to or less than 0.4 is used as the second sacrificial layer 140.

A planarization operation, such as, an etch-back process or CMP, may be performed to planarize the upper surface of the second sacrificial layer 140. By the planarization operation, the upper surface of the gate cap layer 132 is exposed. After the planarization operation, the height $H_{sacr}$ of the second sacrificial layer measured from the surface of the first insulating layer 122 is in a range from about 100 nm to about 350 nm in some embodiments.

FIGS. 4A-4C show views of one of the various stages for manufacturing a FinFET device according to some embodiments of the present disclosure.

The second sacrificial layer 140 is recessed by using wet and/or dry etching, so that a thin layer 141 of the second sacrificial layer remains on the first insulating layer 122 formed on the isolation insulating layer 105. The thickness of the thinned second sacrificial layer 141 is in a range from about 1 nm to about 20 nm in some embodiments. By this recess etching, a portion of the first insulating layer 122 covering the S/D structures 120 and 121 is substantially exposed.

Figures 5A, 5B, 5C:
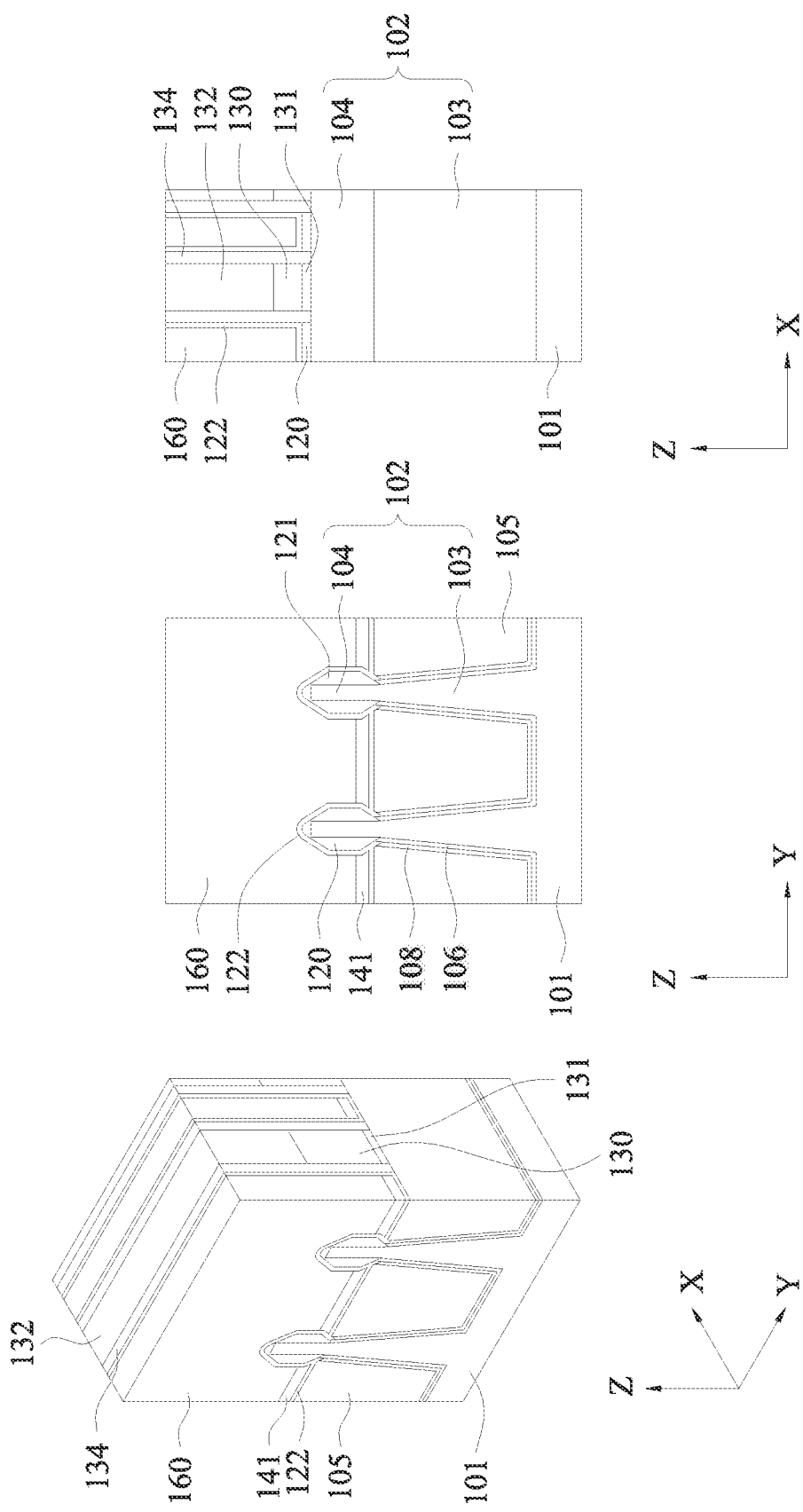
FIGS. 5A-5C illustrate one of the various stages in a semiconductor device fabrication process in accordance with embodiments of the present disclosure.

FIGS. 5A-5C show views of one of the various stages for manufacturing a FinFET device according to some embodiments of the present disclosure.

After the second sacrificial layer 140 is recessed, the third sacrificial layer 160 is formed. The third sacrificial layer 160 is made of a material having a higher (e.g., 5 or more) etching selectivity with respect to the materials of the first insulating layer 122 and/or the isolation insulating layer 105. The third sacrificial layer 160 is made of a different material than the first and second sacrificial layers in some embodiments. In some embodiments, the third sacrificial layer 160 is made of one or more layers of Group IV materials, such as Si, SiGe, SiC, Ge, SiGeC and GeSn, which may be crystalline, polycrystalline or amorphous and may be doped or un-doped. In other embodiments, the third sacrificial layer 160 is made of one or more silicon based dielectric layers of SiOC, SiC, SiON, SiCN, SiOCN, SiN and/or $SiO_2$. Aluminum based dielectric materials, such as aluminum oxide, aluminum oxy-carbide and aluminum oxy-nitride may be used. A SOC (spin-on-carbon) may also be used. In certain embodiments, the third sacrificial layer 160 is made of one or more layers of Group III-V compound semiconductor including, but not limited to, GaAs, GaN, InGaAs, InAs, InP, InSb, InAsSb, AN and/or AlGaN. The third sacrificial layer 160 may be deposited through one or more processes such as PVD, CVD, or ALD, although any acceptable process may be utilized. Other materials and/or processes may be used. A planarization operation, such as, an etch-back process or CMP, may be performed to planarize the upper surface of the third sacrificial layer 160. By the planarization operation, the upper surface of the gate cap layer 132 is exposed. In one embodiment, amorphous or poly Ge is used as the third sacrificial layer 160. In other embodiments, $Si_{1-y}Ge_y$, where y is equal to or more than 0.6 is used as the third sacrificial layer 160.

In one embodiment, amorphous or poly Ge is used as the third sacrificial layer 160. Ge/SiN etching selectivity is more than 10 times the etching electivity of $SiO_2$/SiN. For example, Ge/SiN etching selectivity is about 100 (wet etching), while $SiO_2$/SiN etching electivity is about 3-4. Accordingly, it is possible to remove the Ge third sacrificial layer without causing damages to other layers.

When the second sacrificial layer 140 is made of Si, the Ge third sacrificial layer 160 can be selectively formed on and from the thinned second sacrificial layer 141. In certain embodiments, the second sacrificial layer 140 is made of amorphous Ge or poly Ge and the third sacrificial layer 160 is made of amorphous Si or poly Si.

In certain embodiments, instead of recessing (etching-back) the second sacrificial layer 140 to form the thinned second sacrificial layer 141, a thin layer (about 1 nm to about 20 nm) of amorphous or poly Si is directly formed on the first insulating layer 122 by using CVD or ALD or other suitable film forming methods. Then, the third sacrificial layer 160 (e.g., amorphous or poly Ge) is formed on the thin second sacrificial layer.

Figures 6A, 6B, 6C:
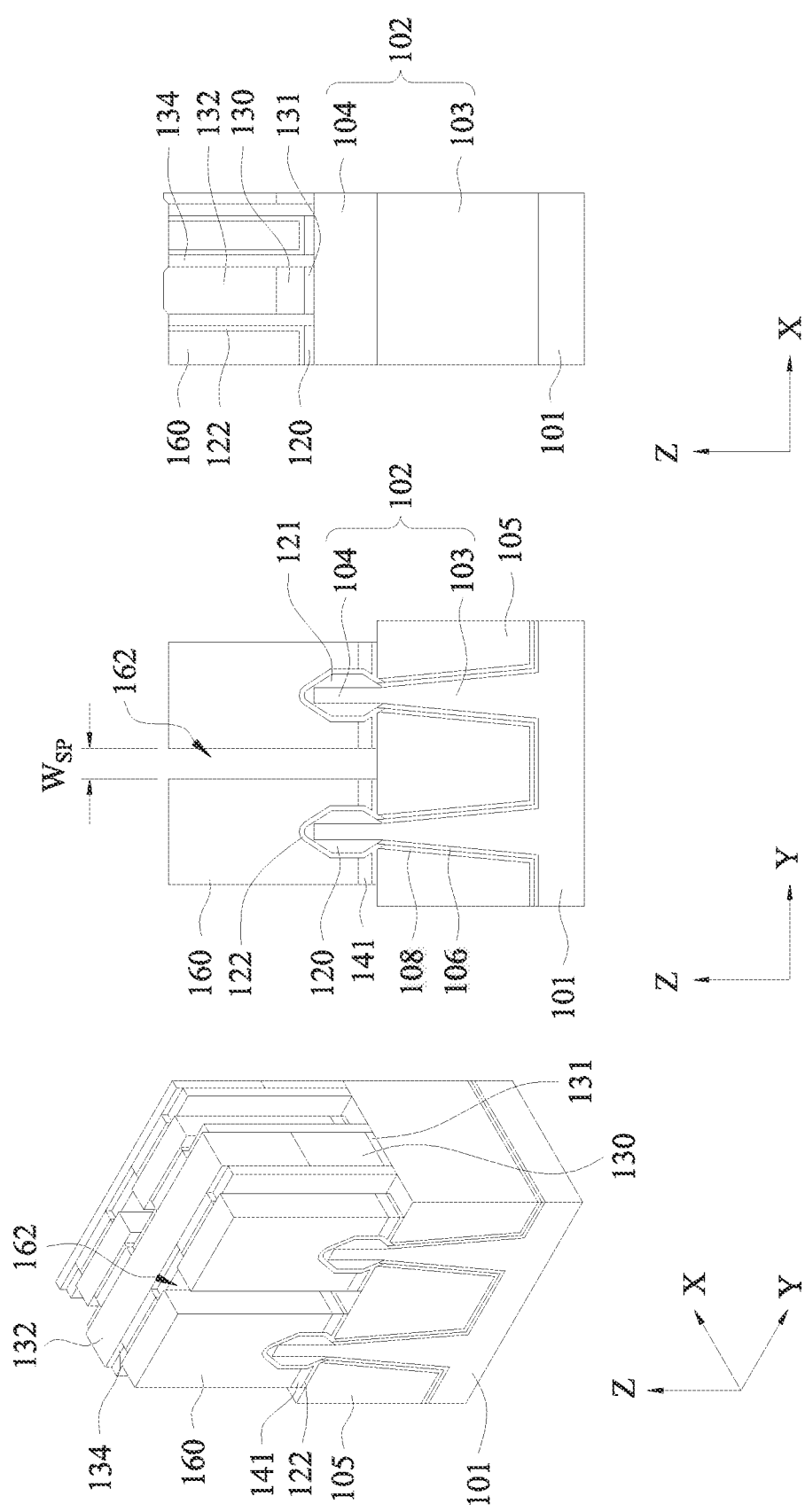
FIGS. 6A-6C illustrate one of the various stages in a semiconductor device fabrication process in accordance with embodiments of the present disclosure.

FIGS. 6A-6C show views of one of the various stages for manufacturing a FinFET device according to some embodiments of the present disclosure.

After the third sacrificial layer 160 is formed, a mask pattern is formed over the third sacrificial layer 160, and by using the mask pattern as an etching mask, the third sacrificial layer 160, the thinned second sacrificial layer 141 and the first insulating layer 122 are patterned, thereby forming openings 162 between the S/D structures 120 and 121. FIGS. 6A-6C show structure after the mask layer is removed.

The mask pattern may be formed by patterning a layer of suitable mask material using a photo-etching operation. The etching operation may include multiple etching processes using different plasma gases. In some embodiments, the mask pattern extends in the X direction over the third sacrificial layer 160 and the gate cap layer 132. The mask pattern is made of one or more layers of dielectric material, such as $SiO_2$, SiN and/or SiON, and/or TiN. The material for the mask pattern may be deposited through one or more processes such as PVD, CVD, or ALD, although any acceptable process may be utilized. Other materials and/or processes may be used.

When a Ge based material (e.g., Ge or SiGe) is used as the third sacrificial layer 160, the etching can be performed by plasma dry etching using, for example, a gas including a fluorocarbon or a gas including a halogen. During the etching, the substrate may be heated at a temperature between about 20° C. to about 200° C. When a Si based material (e.g., poly-Si or amorphous Si) is used as the second sacrificial layer 140, the etching can be performed by plasma dry etching using, for example, a gas including HBr or a gas including $Cl_2$ and $SF_6$. When SOC (spin-on-carbon) is used as the second sacrificial layer 140, the etching can be performed by plasma dry etching using, for example, a gas including $N_2$ and $H_2$ or a gas including $SO_2$ and $O_2$. When a Si oxide based material formed by FCVD is used as the second and/or third sacrificial layers, the etching can be performed by plasma dry etching using, for example, a gas including a fluorocarbon and/or fluorine. In some embodiments, the first insulating layer 122 is not fully etched and remains on the isolation insulating layer 105.

In some embodiments, the opening width $W_{SP}$ in the Y direction is in a range from about 5 nm to about 40 nm, and in a range from about 10 nm to about 40 nm in other embodiments. The width $W_{sp}$ may be other values depending on design rules and/or types of semiconductor devices.

It is noted that as shown in FIGS. 6A and 6C, the gate cap layer 132 is not substantially etched during the patterning of the third sacrificial layer 160, the thinned second sacrificial layer 141. In other words, the material for the gate cap layer 132 has a high etching selectivity (e.g., 5 or more) with respect to the second and third sacrificial layers.

FIGS. 7A-7C show views of one of the various stages for manufacturing a FinFET device according to some embodiments of the present disclosure.

Subsequently, a second insulating layer 146 is formed over the patterned third and second sacrificial layers and the first insulating layer. As shown in FIGS. 7A and 7C, the second insulating layer 146 is also formed on the sidewall spacers 134 and the gate cap layer 132.

In some embodiments, the second insulating layer 146 includes $SiO_2$, SiCN, SiON, SiCN, SiOCN and SiN, but other suitable dielectric materials may be used. In one embodiment, silicon nitride based material, such as SiN, is used. The second insulating layer 146 may be made of a plurality of layers that comprises combinations of the above mentioned materials. The second insulating layer 146 may be deposited through one or more processes such as PVD, CVD, or ALD, although any acceptable process may be utilized. Other materials and/or processes may be used. In some embodiments, the second insulating layer 146 has a thickness between about 1 nm and about 10 nm. Other thicknesses are used in other embodiments.

FIGS. 8A-8C show views of one of the various stages for manufacturing a FinFET device according to some embodiments of the present disclosure.

After the second insulating layer 146 is formed, a first interlayer dielectric (ILD) layer 145 is formed to fill the openings 162 and over the third sacrificial layer 160.

The ILD layer 145 may include a single layer or multiple layers. In some embodiments, the ILD layer 145 includes $SiO_2$, SiCN, SiOC, SiON, SiOCN, SiN or a low-k material, but other suitable dielectric film may be used. The ILD layer 145 may be formed by CVD, PECVD or ALD, FCVD, or a spin-on-glass process. A planarization process, such as a CMP process, may be performed to remove excess materials. By the planarization process, the upper surface of the third sacrificial layer 160 (and the cap insulation layer 132) is exposed in some embodiments.

FIGS. 9A-9C show views of one of the various stages for manufacturing a FinFET device according to some embodiments of the present disclosure.

Subsequently, the third sacrificial layer 160 is removed, thereby forming contact openings 148 and 149 to expose the S/D structure 120, 121 covered by the first insulating layer 122. The etching operation to remove the third sacrificial layer 160 may be isotropic or anisotropic. Further, the first insulating layer 122 is removed, thereby exposing the S/D structures 120, 121.

When a Ge based material (e.g., Ge or SiGe) is used as the third sacrificial layer 160, the etching can be performed by plasma dry etching using, for example, ozone or wet etching using a solution containing $NH_4OH$ and $H_2O_2$ or a solution containing HCl and $H_2O_2$. The remaining first insulating layer 122 can be removed by using a suitable etching operation.

When a Si based material (e.g., poly-Si or amorphous Si) is used as the second sacrificial layer 140, the etching can be performed by plasma dry etching using a gas including $Cl_2$ and $NF_3$ or a gas including $F_2$, or wet etching using $NH_4OH$ and/or tetramethylammonium (TMAH). When SOC (spin-on-carbon) is used as the second sacrificial layer 140, the etching can be performed by plasma dry etching using, for example, a gas including $N_2$ and $H_2$ or a gas including $SO_2$ and $O_2$. When a Si oxide based material formed by FCVD is used as the second and/or third sacrificial layers, the etching can be performed by wet etching using, for example, HF or buffered HF (BHF).

The width $W_{CH}$ along the Y direction of the openings 148, 149 is in a range from about 20 nm to about 100 nm in some embodiments.

FIGS. 10A-10C show views of one of the various stages for manufacturing a FinFET device according to some embodiments of the present disclosure.

After the second and third sacrificial layers are removed and the first insulating layer 122 formed on the S/D structures 120, 121 are removed, a conductive material is filled in the contact openings 148, 149, thereby forming S/D contacts 150.

In some embodiments, a silicide layer is formed on the exposed S/D structures 120, 121. The metal silicide formation process may form a metal silicide on the side portions of the S/D structures. The metal silicide formation process includes a metal film deposition on the S/D structures, a thermal treatment to form a metal silicide at the interface or surface of the S/D structures, and an etching process to remove the excess unreacted metal. The metal silicide comprises $TiSi_x$, $NiSi_x$, $CoSi_x$, $NiCoSi_x$, and $TaSi_x$, but other suitable silicide materials may be used. In some embodiments, the silicide layer has a thickness between about 0.5 nm and about 10 nm. In other embodiments, a silicide layer is not formed at this stage of the manufacturing operations, and may be formed at an earlier manufacturing stage, e.g., before forming the first insulating layer 122. The metal films not formed on the S/D epitaxial layer and the metal films not consumed to form the silicide layer are removed by suitable etching operation in some embodiments. In other embodiments, the metal films are not removed and remain.

The S/D contacts 150 may include a single layer or a multi-layer structure. For example, in some embodiments, the contact 150 includes a contact liner layer, such as a diffusion barrier layer, an adhesion layer, or the like, and a contact body formed over the contact liner layer in the contact openings 148, 149. The contact liner layer may include Ti, TiN, Ta, TaN, or the like formed by ALD, CVD, or the like. The contact body may be formed by depositing a conductive material, such as one or more layers of Ni, Ta, TaN, W, Co, Ti, TiN, Al, Cu, Au, alloys thereof, combinations thereof, or the like, but other suitable metals may also be used. A planarization process, such as a CMP, may be performed to remove excess material from a surface of the ILD layer 145.

After the S/D contact 150 is formed, the height Hg of the gate structure including the gate cap layer 132 measured from the top of the fin structure 104 is in a range from about 20 nm to 100 nm and the height $H_{mg}$ of the metal gate 130 measured from the top of the fin structure 104 is in a range from about 10 nm to about 60 nm in some embodiments.

After forming the contact 150, further CMOS processes are performed to form various features such as additional interlayer dielectric layers, contacts/vias, interconnect metal layers, and passivation layers, etc.

FIGS. 11A-21C illustrate various processes in a semiconductor device fabrication process in accordance with other embodiments of the present disclosure. In FIGS. 11A-21C, the "A" figures (e.g., FIGS. 11A, 12A, etc.) illustrate a perspective view, the "B" figures (e.g., FIGS. 11B, 12B, etc.) illustrate a cross-sectional view along the Y direction corresponding to line Y1-Y1 illustrated in FIGS. 11A and 12A, and the "C" figures (e.g., FIG. 11C, 12C, etc.) illustrate a cross-sectional view along the X direction corresponding to line X1-X1 illustrated in FIGS. 11A and 12A It is understood that additional operations can be provided before, during, and after processes shown by FIGS. 11A-21C, and some of the operations described below can be replaced or eliminated, for additional embodiments of the method. The order of the operations/processes may be interchangeable. Material, configuration, dimensions and/or processes the same as or similar to the foregoing embodiments described with respect to FIGS. 1A-10C may be employed in the following embodiments, and detailed explanation thereof may be omitted.

Figures 11A, 11B, 11C:
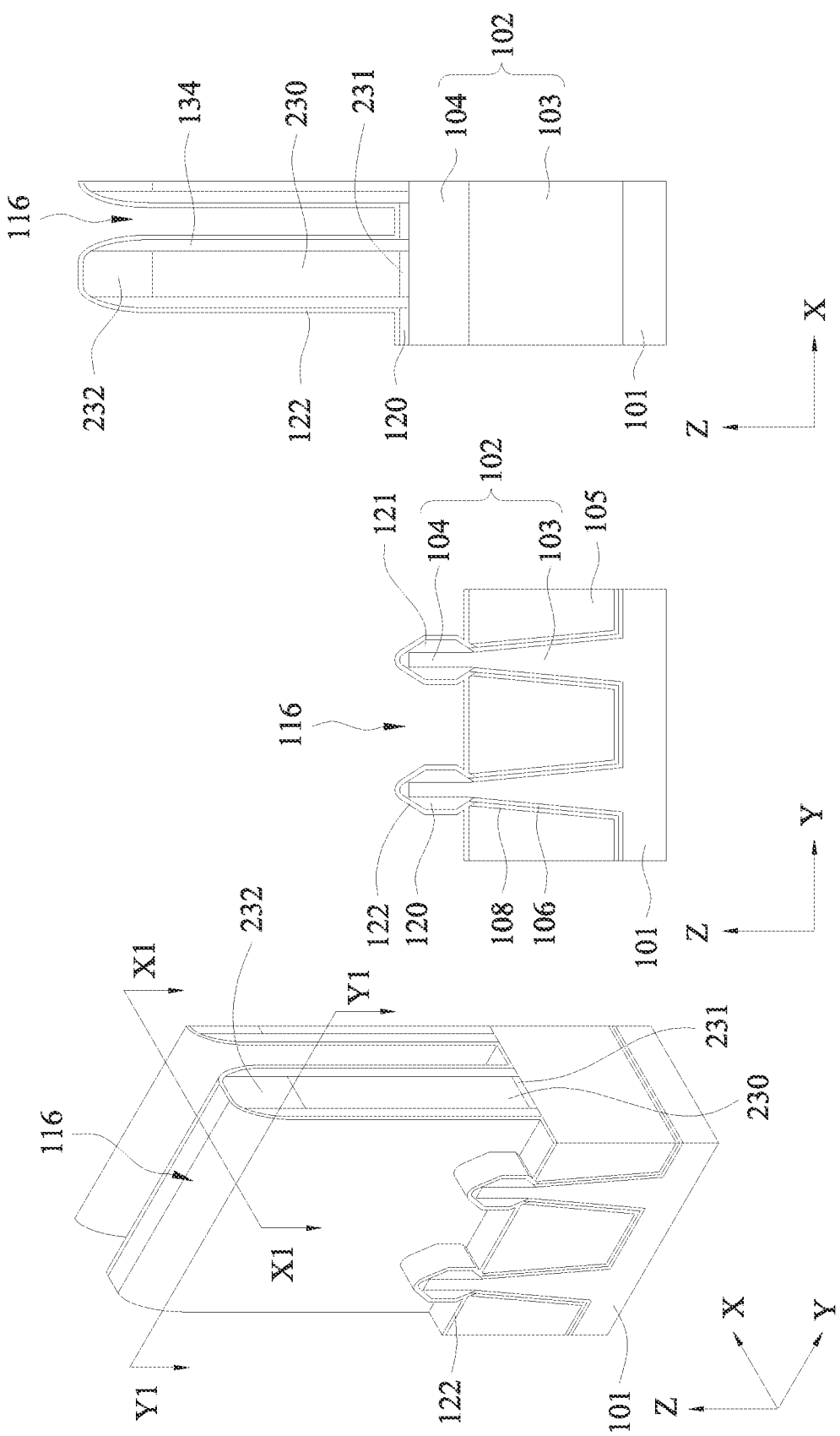
FIGS. 11A-11C illustrate one of the various stages in a semiconductor device fabrication process in accordance with other embodiments of the present disclosure.

FIGS. 11A-11C show views of one of the various stages for manufacturing a FinFET device according to some embodiments of the present disclosure.

The structure shown in FIGS. 11A-11C is substantially similar to the structure shown in FIGS. 2A-2C, except that the gate structure has not been formed and a dummy gate electrode 230, a dummy gate dielectric layer 213 and a gate mask layer 232 are disposed instead of the gate electrode 130, the gate dielectric layer 131 and gate cap layer 132. The operations to fabricate the dummy gate structures are as set forth above.

FIGS. 12A-12C show views of one of the various stages for manufacturing a FinFET device according to some embodiments of the present disclosure.

Similar to FIGS. 3A-3C, a second sacrificial layer 140 is formed in the openings 116.

Figures 13A, 13B, 13C:
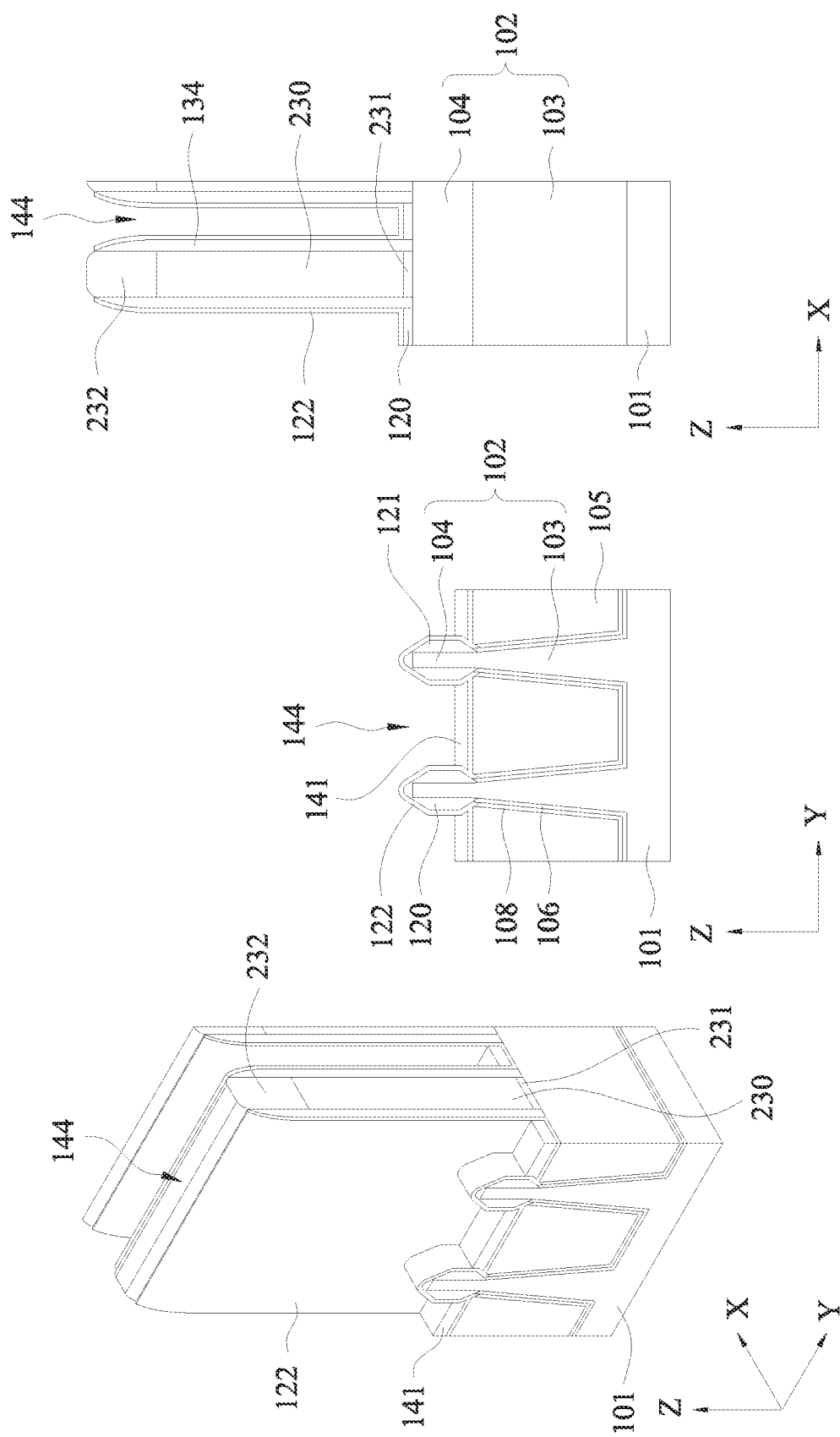
FIGS. 13A-13C illustrate one of the various stages in a semiconductor device fabrication process in accordance with other embodiments of the present disclosure.

FIGS. 13A-13C show views of one of the various stages for manufacturing a FinFET device according to some embodiments of the present disclosure.

Similar to FIGS. 4A-4C, the second sacrificial layer 140 is recessed to form a thinned second sacrificial layer 141, thereby forming openings 144.

FIGS. 14A-14C show views of one of the various stages for manufacturing a FinFET device according to some embodiments of the present disclosure.

Similar to FIGS. 5A-5C, a third sacrificial layer 160 is formed in the openings 144.

FIGS. 15A-15C show views of one of the various stages for manufacturing a FinFET device according to some embodiments of the present disclosure.

Subsequently, the third sacrificial layer 160 is partially recessed to a level of the middle portion of the dummy gate electrode 122 in the Z direction, thereby forming openings 164. The third sacrificial layer 160 can be recessed by an etch-back process and/or wet etching. The remaining thickness $H_{sc}$ of the recessed third sacrificial layer 160 is in a range from about 40 nm to about 200 nm in some embodiments.

FIGS. 16A-16C show views of one of the various stages for manufacturing a FinFET device according to some embodiments of the present disclosure.

The openings 164 are filled with an insulating material, thereby forming a mask layer 220. In some embodiments, the mask layer 220 is made of one or more layers of SiOC, SiC, SiON, SiCN, SiOCN, SiN and/or $SiO_2$. In one embodiment, SiN is used. The mask layer 220 may be deposited through one or more processes such as PVD, CVD, or ALD, although any acceptable process may be utilized. Other materials and/or processes may be used. A planarization operation, such as, an etch-back process or CMP, may be performed to planarize the upper surface of the mask layer and gate mask layer 232. By the planarization operation, the upper surface of the dummy gate electrode layer 230 is exposed.

FIGS. 17A-17C show views of one of the various stages for manufacturing a FinFET device according to some embodiments of the present disclosure.

Subsequently, the dummy gate electrode 230 and the dummy gate dielectric layer 231 are removed, thereby forming an opening 235. The removal operations are explained above with respect to FIGS. 1A-1C.

Figures 18A, 18B, 18C:
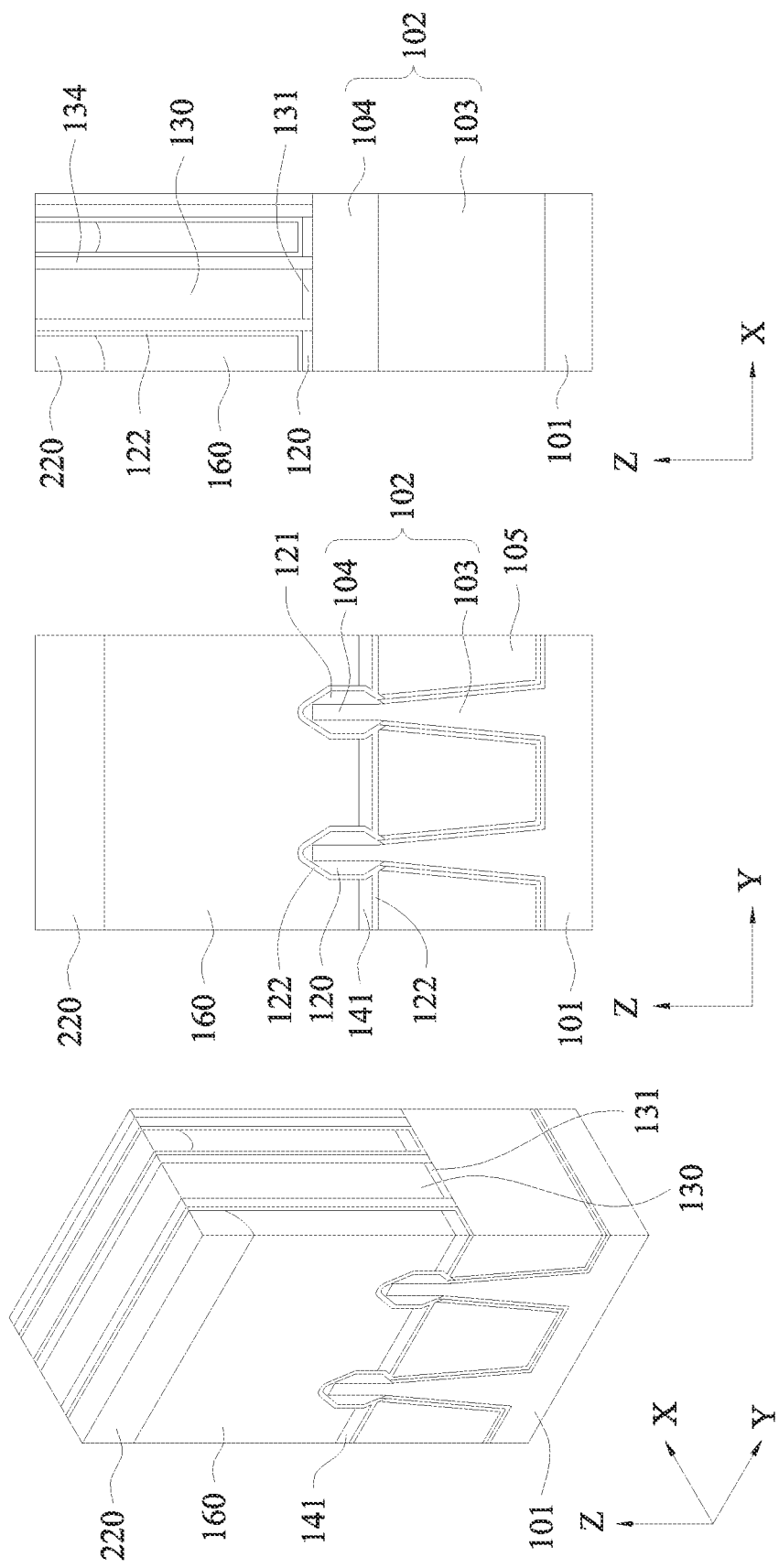
FIGS. 18A-18C illustrate one of the various stages in a semiconductor device fabrication process in accordance with other embodiments of the present disclosure.

FIGS. 18A-18C show views of one of the various stages for manufacturing a FinFET device according to some embodiments of the present disclosure.

After the dummy gate structure is removed, a gate dielectric layer 131 is formed over a channel region of the fin structure 104, and a conductive layer for a gate electrode 130 is formed on the gate dielectric layer 131. The gate formation operations are explained above with respect to FIGS. 1A-1C.

The gate electrode 130 may be formed using a suitable process such as ALD, CVD, PVD, plating, or combinations thereof. A planarization process, such as a CMP, may be performed to remove excess materials. After the planarization operation the mask layer 220 is exposed.

Figures 19A, 19B, 19C:
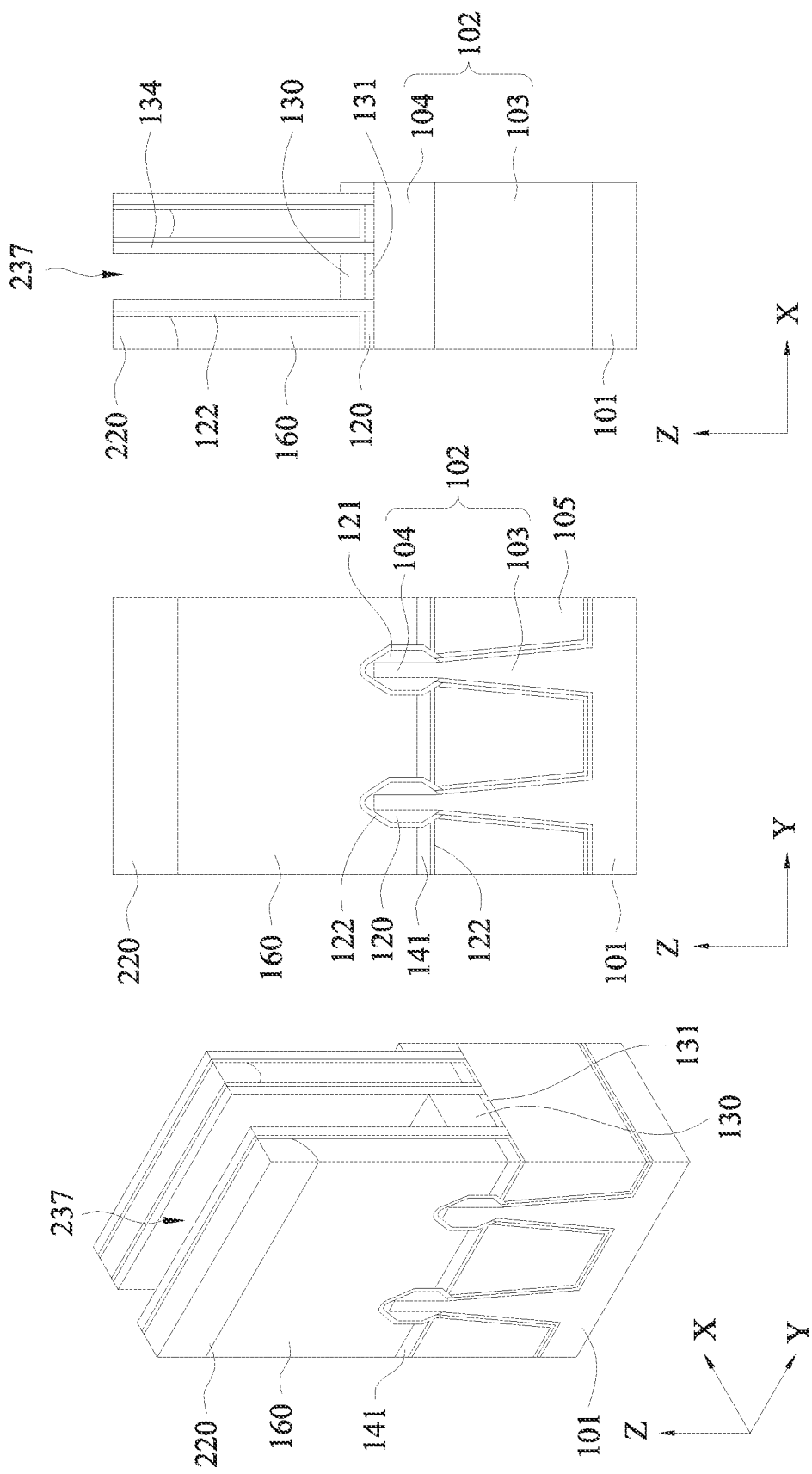
FIGS. 19A-19C illustrate one of the various stages in a semiconductor device fabrication process in accordance with other embodiments of the present disclosure.

FIGS. 19A-19C show views of one of the various stages for manufacturing a FinFET device according to some embodiments of the present disclosure.

Subsequently, the gate electrode layer is recessed, thereby forming the gate electrode 130 and a gate cap opening 237.

FIGS. 20A-20C show views of one of the various stages for manufacturing a FinFET device according to some embodiments of the present disclosure.

Then, an insulating layer 132 is formed in the gate cap opening 237 and over the mask layer 220. In some embodiments, the insulating layer for the gate cap layer 132 includes $SiO_2$, SiCN, SiON, SiN, $Al_2O_3$, $La_2O_3$, a combination thereof, or the like, but other suitable dielectric films may be used. The insulating layer for the gate cap layer 132 may be formed using, for example, CVD, PVD, spin-on, or the like. Other suitable process steps may be used.

FIGS. 21A-21C show views of one of the various stages for manufacturing a FinFET device according to some embodiments of the present disclosure.

Subsequently, a planarization process, such as a CMP, may be performed to remove excess materials, thereby forming the gate cap layer 132.

The structure of FIGS. 21A-21C is substantially the same as the structure of FIGS. 5A-5C. Subsequently, the same operations as explained with FIGS. 6A-10C are performed.

Figure 22B:
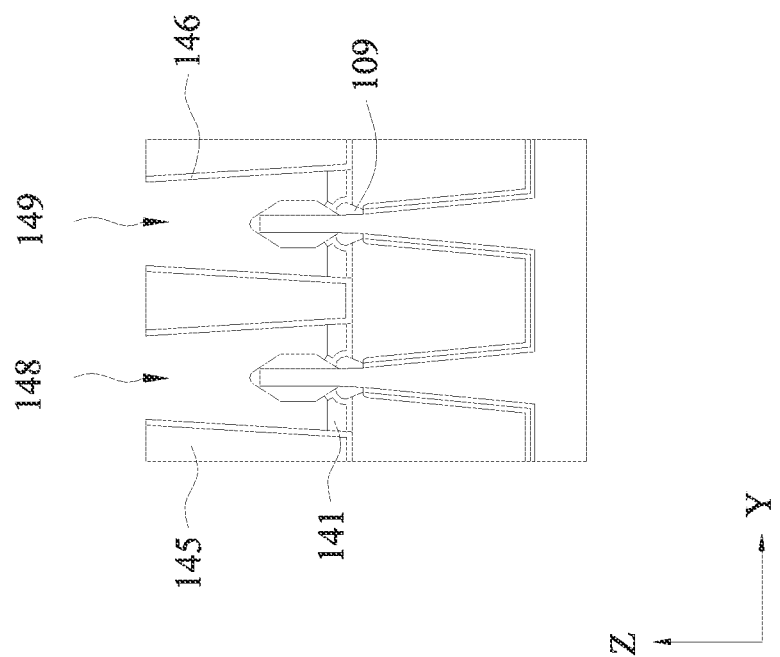
FIGS. 22A and 22B illustrate views of a semiconductor device in accordance with some embodiments of the present disclosure.
Figure 22A:
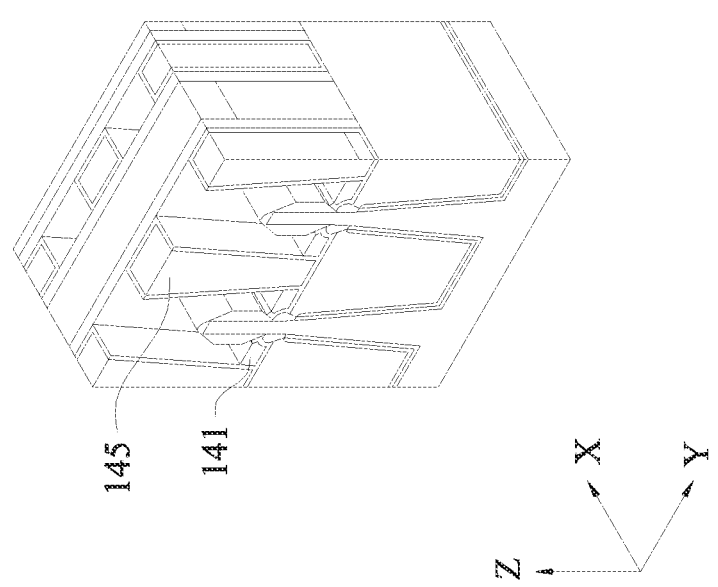
Figure 23B:
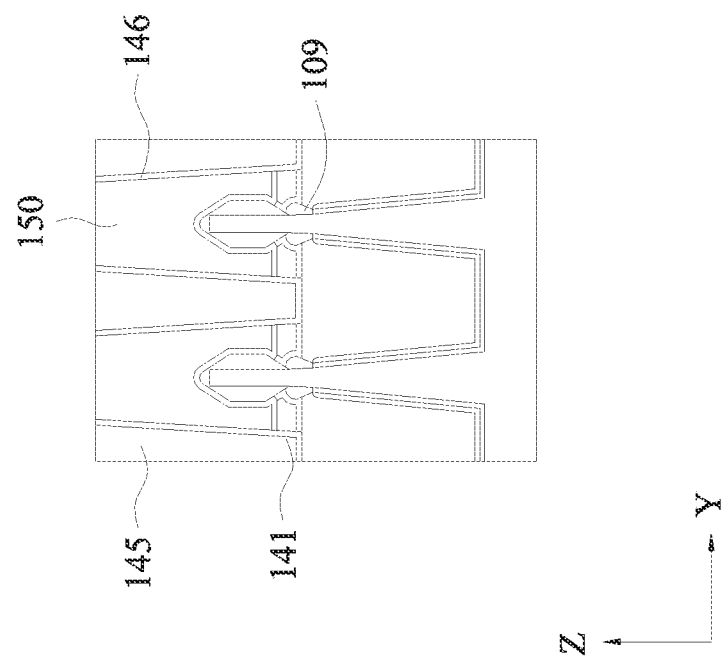
FIGS. 23A and 23B illustrate views of a semiconductor device in accordance with some embodiments of the present disclosure.

FIGS. 22A and 23B illustrate views of a semiconductor device in accordance with some embodiments of the present disclosure.

In some embodiments of the present disclosure, before epitaxial layers are formed to form the S/D structure 120, 122, the upper portion of the fin 104 corresponding to the S/D region is covered by a cover layer made of, for example, SiN, and then the cover layer is removed from the fin 104 and then the epitaxial layers are formed. In such a case, the cover layer 109 remains at the bottom portion of the fin 104. The epitaxial layers for the S/D structure 120, 122 are formed on the fin 104 not covered by the cover layer 109.

When recessing the second sacrificial layer 140, the second sacrificial layer 140 is recessed to the level of the epitaxial layers for the S/D structure 120, 122. In other words, the thinned second sacrificial layer 141 has a thickness such that the upper surface of the thinned sacrificial layer is in contact with the S/D structure 120, 122 or is equal to the bottom of the S/D structure 120, 122.

Figure 23A:
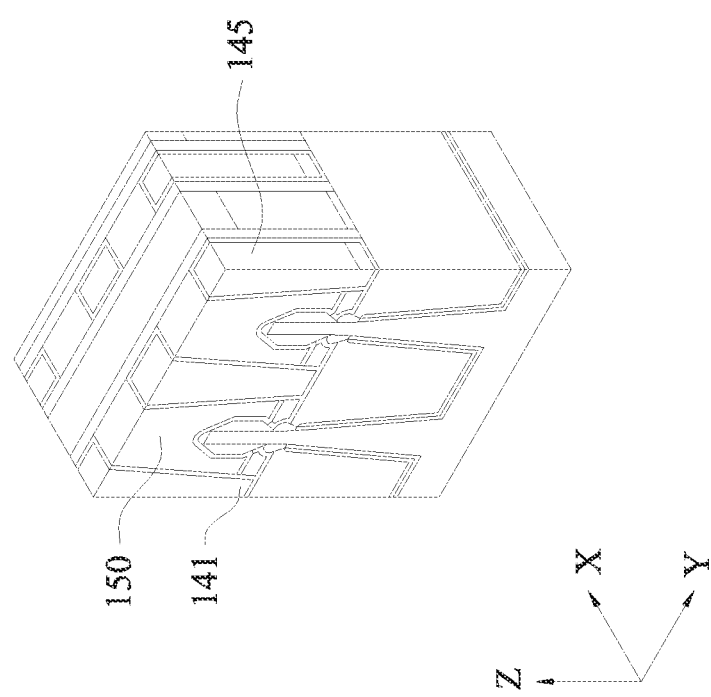

When the openings 148 and 149 are formed (see, FIGS. 9A-9C), the thinned second sacrificial layer 141 is not etched or is only partially etched. Thus, as shown in FIG. 23A, the second sacrificial layer 141 remains under the S/D contact 150.

FIGS. 24A-24C illustrate views of a semiconductor device in accordance with some embodiments of the present disclosure.

FIG. 24A is substantially the same as FIG. 23B, where the thinned second sacrificial layer 141 remains to or higher than the bottom of the S/D structure 120, 122. In some embodiments, the thickness $T_{ge}$ of the thinned second sacrificial layer 141 is in a range from about 0 nm to about 45 nm. The thinned second sacrificial layer may be equal to or higher or lower than bottom of the S/D structure 120, 122.

As shown in FIG. 24B, the thinned second sacrificial layer 141 remains below the bottom of the S/D structure 120, 122. In some embodiments, the thickness $T_{ge}$ of the thinned second sacrificial layer 141 is in a range from about 0 nm to about 45 nm. The thinned second sacrificial layer may be equal to or higher or lower than bottom of the S/D structure 120, 122. In other embodiments, no second sacrificial layer 141 remains as shown in FIG. 24C.

Further, due to the etching properties of the third sacrificial layer etching, the opening 162 has a tapered shape having an upper width larger than a bottom width in some embodiments. Accordingly, the openings 148 and 149 have a reverse tapered shape having a upper width smaller than a bottom width, as shown in FIG. 22B, and then the S/D contact 150 also has a reverse tapered shape, as shown in FIG. 23B.

FIGS. 25A-25C illustrate views of a semiconductor device in accordance with some embodiments of the present disclosure. FIG. 25B is a cross sectional view corresponding to line X2-X2 of FIG. 25A and FIG. 25C is a cross sectional view corresponding to line X1-X1 of FIG. 25A.

During the formation of the openings 162 (see, FIGS. 6A-6C), the upper portion of the gate cap layer 132 is slightly etched in some embodiments. Accordingly, as shown in FIG. 25B, the upper portion of the ILD layer 145 between the S/D structures 120 and 121 has a funnel shape having a wider top than a body region along the X direction.

During the formation of the openings 148 and 149 (see, FIGS. 9A-9C), the upper portion of the gate cap layer 132 and the sidewall spacers 134 are slightly etched in some embodiments. Accordingly, as shown in FIG. 25C, the upper portion of the S/D contact 150 has a funnel shape having a wider top than a body region along the X direction.

In some embodiments, Ge is used as the third sacrificial layer 160. Accordingly, Ge element diffuses into the second insulating layer 146 and/or ILD layer 145, and Ge element (or in the form of GeO (germanium oxide)) can be found in or on the second insulating layer 146 and/or ILD layer 145.

It will be understood that not all advantages have been necessarily discussed herein, no particular advantage is required for all embodiments or examples, and other embodiments or examples may offer different advantages.

For example, in the present disclosure, since material having a higher etching selectivity (e.g., Ge) with respect to insulating layers (e.g., silicon oxide based material, silicon nitride based material) is used as the second and third sacrificial layers, it is possible to more precisely control the size of the S/D structures and the S/D contact structure. With these manufacturing methods, the material can easily fill the space between sidewall spacers to form a void-free film. Further, the full space between sidewall spacer can be fully used for S/D contacts and less damage is caused to the contact regions. Since the area of the S/D contacts is wider, it is possible to form a wrap-around contact to gain contact area by higher selective etching to the silicon oxide and/or nitride. By the foregoing structures and methods, it is possible to avoid an S/D epitaxial layer from being damaged and to form wrap-around contact structures.

In accordance with an aspect of the present disclosure, in a method of forming a semiconductor device including a fin field effect transistor (FinFET), a first sacrificial layer is formed over a source/drain structure of a FinFET structure and an isolation insulating layer. The first sacrificial layer is recessed so that a remaining layer of the first sacrificial layer is formed on the isolation insulating layer and an upper portion of the source/drain structure is exposed. A second sacrificial layer is formed on the remaining layer and the exposed source/drain structure. The second sacrificial layer and the remaining layer are patterned, thereby forming an opening. A dielectric layer is formed in the opening. After the dielectric layer is formed, the patterned first and second sacrificial layers are removed to form a contact opening over the source/drain structure. A conductive layer is formed in the contact opening.

In accordance with another aspect of the present disclosure, in a method of forming a semiconductor device including fin field effect transistors (FinFETs), a first sacrificial layer is formed over a first source/drain structure of a first FinFET structure, a second source/drain structure of a second FinFET structure and an isolation insulating layer. The first source/drain structure is disposed adjacent to the second source/drain structure. The first sacrificial layer is recessed so that a remaining layer of the first sacrificial layer is formed on the isolation insulating layer and upper portions of the first and second source/drain structures are exposed. The second sacrificial layer is formed on the remaining layer and the exposed first and second source/drain structures. The second sacrificial layer and the remaining layer are patterned, thereby forming an opening between the first source/drain structure and the second source/drain structure. A dielectric layer is formed in the opening. After the dielectric layer is formed, the patterned first and second sacrificial layers are removed to form a first contact opening over the first source/drain structure and a second contact opening over the second source/drain structure. A first conductive layer is formed in the first contact opening and a second conductive layer in the second contact opening.

In accordance with another aspect of the present disclosure, a semiconductor device including fin field effect transistors (FinFETs), includes first and second FinFETs and a dielectric layer. The first FinFET includes a first fin structure extending in a first direction, a first source/drain structure and a first source/drain contact in contact with the first source/drain structure. The second FinFET is disposed adjacent to the first FinFET and includes a second fin structure extending in the first direction, a second source/drain structure and a second source/drain contact in contact with the second source/drain structure. The dielectric layer separates the first source/drain structure and the second source/drain structure. The dielectric layer is made of silicon-based insulating material, and contains Ge at or near an interface between the dielectric layer and one of the first and second source/drain contacts.

The foregoing outlines features of several embodiments or examples so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments or examples introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A semiconductor device, comprising:
 a fin structure extending in a first direction;
 an isolation insulating layer from which the fin structure protrudes;
 a source/drain epitaxial layer disposed over the fin structure;
 a source/drain contact in contact with the source/drain epitaxial layer; and
 a gate structure extending in a second direction crossing the first direction and including a gate electrode and a gate cap insulating layer,
 wherein in a cross section cutting the fin structure along the first direction, the source/drain contact has a top width greater than a bottom width, and
 in a cross section along the first direction, opposite sides of a top of the gate cap insulating layer are recessed such that a top width of the gate cap insulating layer is smaller than a bottom width of the gate cap insulating layer.

2. The semiconductor device of claim 1, wherein the source/drain contact is in contact with the gate cap insulating layer.

3. The semiconductor device of claim 1, further comprising a gate sidewall spacer disposed on a sidewall of the gate structure.

4. The semiconductor device of claim 3, wherein the gate sidewall spacer only partially covers a sidewall of the gate cap insulating layer.

5. The semiconductor device of claim 1, further comprising a dielectric layer disposed at a side of the gate structure in the first direction and at a side of the source/drain contact in the second direction.

6. The semiconductor device of claim 5, wherein in a cross section along the first direction, the dielectric layer has a top width greater than a bottom width.

7. The semiconductor device of claim 5, wherein the dielectric layer includes a first dielectric layer in contact with the source/drain contact and a second dielectric layer disposed on the first dielectric layer and separated from the source/drain contact by the first dielectric layer.

8. The semiconductor device of claim 7, wherein the second dielectric layer is in contact with the gate cap insulating layer.

9. The semiconductor device of claim 7, wherein the second dielectric layer comprises a silicon nitride based material.

10. The semiconductor device of claim 9, wherein the second dielectric layer further comprises GeO.

11. The semiconductor device of claim 7, wherein the first dielectric layer comprises GeO.

12. A semiconductor device, comprising:
 a first FinFET including a first fin structure, a first source/drain epitaxial layer, a first source/drain contact disposed over the first source/drain epitaxial layer;
 a second FinFET disposed adjacent to the first FinFET and including a second fin structure, a second source/drain epitaxial layer and a second source/drain contact disposed over the second source/drain epitaxial layer; and
 a dielectric layer separating the first source/drain contact and the second source/drain contact, wherein:
 the first and second fin structures extend in a first direction,
 the first FinFET and the second FinFET share a gate structure extending in a second direction crossing the first direction and including a gate electrode layer and a gate cap insulating layer,
 in a cross section cutting the first fin structure along the first direction, the first source/drain contact has a funnel shape having a wider top than a body region, and
 in a cross section of the first FinFET along the first direction, opposite sides of a top of the gate cap insulating layer are recessed such that a top width of the gate cap insulating layer is smaller than a bottom width of the gate cap insulating layer.

13. The semiconductor device of claim 12, wherein in a cross section cutting the dielectric layer along the first direction, the dielectric layer has a funnel shape having a wider top than a body region.

14. The semiconductor device of claim 12, wherein the dielectric layer includes a first dielectric layer in contact with the first and second source/drain contacts and a second dielectric layer disposed on the first dielectric layer.

15. The semiconductor device of claim 14, wherein the second dielectric layer is in contact with the gate cap insulating layer.

16. The semiconductor device of claim 14, wherein the second dielectric layer comprises a silicon nitride based material.

17. The semiconductor device of claim 16, wherein the second dielectric layer further comprises GeO.

18. The semiconductor device of claim 14, wherein the first dielectric layer comprises GeO.

19. A semiconductor device, comprising:
 a first FinFET including a first fin structure, a first gate structure, a first source/drain epitaxial layer, a first source/drain contact disposed over the first source/drain epitaxial layer;
 a second FinFET disposed adjacent to the first FinFET and including a second fin structure, a second gate structure, a second source/drain epitaxial layer and a second source/drain contact disposed over the second source/drain epitaxial layer; and
 a dielectric layer separating the first source/drain contact and the second source/drain contact, wherein:
 the first and second fin structures extend in a first direction,
 the first and second gate structures extend in a second direction crossing the first direction,
 in a cross section cutting the first fin structure along the first direction, the first source/drain contact has a funnel shape having a wider top than a body region, and in a cross section of the first FinFET along the first direction, opposite sides of a top of a gate cap insulating layer are recessed such that a top width of the gate cap insulating layer is smaller than a bottom width of the gate cap insulating layer.

20. The semiconductor device of claim 19, wherein the dielectric layer comprises germanium.

* * * * *